United States Patent
Omata et al.

(10) Patent No.: US 7,565,841 B2
(45) Date of Patent: Jul. 28, 2009

(54) OPERATING FREQUENCY SELECTION METHOD FOR HARDNESS MEASUREMENT SYSTEM, OPERATING FREQUENCY SELECTION APPARATUS, AND HARDNESS MEASUREMENT SYSTEM

(75) Inventors: Sadao Omata, Tokyo (JP); Yoshinobu Murayama, Tokyo (JP); Katsuhito Honda, Fukushima (JP)

(73) Assignee: Nihon University, Tokyo (JP)

( * ) Notice: Subject to any disclaimer, the term of this patent is extended or adjusted under 35 U.S.C. 154(b) by 91 days.

(21) Appl. No.: 11/547,446

(22) PCT Filed: Dec. 13, 2004

(86) PCT No.: PCT/JP2004/018577

§ 371 (c)(1),
(2), (4) Date: Apr. 30, 2007

(87) PCT Pub. No.: WO2005/100951

PCT Pub. Date: Oct. 27, 2005

(65) Prior Publication Data

US 2007/0250294 A1     Oct. 25, 2007

(30) Foreign Application Priority Data

Apr. 7, 2004    (JP) .............................. 2004-112704

(51) Int. Cl.
*G01N 29/00*    (2006.01)
*G01N 3/48*    (2006.01)

(52) U.S. Cl. ................................ 73/573; 73/602; 73/81

(58) Field of Classification Search ................... 73/573, 73/579, 602, 629, 81, 83, 85
See application file for complete search history.

(56) References Cited

U.S. PATENT DOCUMENTS

| 4,646,571 A | * | 3/1987 | Kising et al. ................... 73/573 |
| 5,092,175 A | * | 3/1992 | Winckler et al. .............. 73/573 |
| 5,216,921 A | * | 6/1993 | Tsuboi ........................ 73/579 |
| 5,766,137 A | | 6/1998 | Omata |
| 6,539,781 B1 | * | 4/2003 | Crezee .......................... 73/81 |
| 6,854,331 B2 | * | 2/2005 | Omata ......................... 73/573 |

FOREIGN PATENT DOCUMENTS

| JP | A 9-145691 | 6/1997 |
| JP | A 2001-275995 | 10/2001 |

OTHER PUBLICATIONS

Yoshinobu Murayama et al., "Fabrication of Micro Tactile Sensor for the Measurement of Micro-Scale Local Elasticity," Sensors and Actuators A 109, Issue 3, pp. 202-207, Jan. 1, 2004.

* cited by examiner

*Primary Examiner*—Helen C. Kwok
(74) *Attorney, Agent, or Firm*—Oliff & Berridge, PLC

(57) ABSTRACT

In a hardness measurement system, selecting an operating frequency is facilitated by using a phase shift circuit. A hardness sensor is connected to an operating frequency selection apparatus and in a free end state the amplitude versus frequency characteristic is acquired, and the frequency and the phase of the peaks are measured and acquired as the free end characteristic. Next, the hardness sensor is placed into contact with a first test piece, and the frequency and the phase that change for the peaks are measured and acquired as the first characteristic. The same procedure is performed for a second test piece that is harder than the first test piece to yield the second characteristic. Based on these characteristics and a predetermined selection criterion a peak suitable for hardness measurement is selected and the operating frequency is set from the frequency of the peak.

20 Claims, 12 Drawing Sheets (a)           (b)           (c)

Fig. 5

|  | TYPE 1 | TYPE 2 | TYPE 3 | TYPE 4 |
|---|---|---|---|---|
| AMPLITUDE | ↓ | ↓ | ↑ | ↑ |
| FREQUENCY | ↑ | ↑ | ↓ | ↓ |
| PHASE | ↑ | ↓ | ↑ | ↓ |

Fig. 6

|  | (FREE END CHARACTERISTIC ↓ FIRST CHARACTERISTIC) TYPE 4 | (FREE END CHARACTERISTIC ↓ SECOND CHARACTERISTIC) TYPE 1 |
|---|---|---|
| FREQUENCY | ↓ | ↑ |
| PHASE | ↓ | ↑ | ns
OPERATING FREQUENCY SELECTION METHOD FOR HARDNESS MEASUREMENT SYSTEM, OPERATING FREQUENCY SELECTION APPARATUS, AND HARDNESS MEASUREMENT SYSTEM

BACKGROUND OF THE INVENTION

1. Field of the Invention

The present invention relates to the selection of an operating frequency for a hardness measurement system for measuring the hardness of a test object using a hardness sensor having a vibrator for applying vibrations to an object and a vibration detection sensor for detecting signals reflected from the object, and more particularly to a method for selecting the operating frequency and an operation frequency selection apparatus for the hardness measurement system for measuring the hardness of an object from frequency changes that occur according to the hardness of the object and including a phase shift circuit, which is connected in series with an amplifier to the hardness sensor, to change the frequency and to shift the phase difference to zero when a phase difference occurs between an input waveform to the vibrator and an output waveform from the vibration detection sensor.

2. Description of the Related Art

One method for measuring the hardness of living tissue includes pressing a probe against the tissue to be measured, applying vibrations, and obtaining a characteristic value corresponding to the hardness from frequency changes and phase changes by detecting the mechanical vibration response of the living tissue with respect to the input vibrations. In particular, as disclosed in Japanese Patent Laid-Open Publication No. Hei 9-145691, the present inventor has devised a hardness measurement system for measuring the hardness of an object from frequency changes that occur according to the hardness of the object by using a hardness sensor that includes a vibrator for applying vibrations to an object and a vibration detection sensor for detecting signals reflected from the object and a phase shift circuit, which is connected in series with an amplifier to the hardness sensor, to change the frequency and to shift the phase difference to zero when a phase difference occurs between an input waveform to the vibrator and an output waveform from the vibration detection sensor.

An example of a hardness measurement system using a phase shift circuit is shown in FIG. 8. In FIG. 8, a hardness measurement system 10 includes a hardness sensor 12 to be pressed against an object 8, such as living tissue, and a hardness detection part 20. The hardness sensor 12 includes a vibrator 14 for applying vibrations to the object 8 and a vibration detection sensor 16 for detecting signals reflected from the object 8. For this hardness sensor 12, two stacked piezoelectric elements can be used, with one used as the vibrator 14 and the other used as the vibration detection sensor 16. The hardness detection part 20 includes an appropriate DC blocking capacitor, an amplifier 22, and a phase shift circuit 24 connected in series between the output terminal from the vibration detection sensor 16 and the input terminal to the vibrator 14, a frequency deviation detector 26 for detecting the frequency deviation that occurs for compensating for the phase difference by the phase shift circuit 24, and a hardness converter 28 for converting the detected frequency deviation and outputting a hardness value. The frequency deviation detector 26 can use a general frequency counter and the hardness converter 28 can use a microcomputer to perform conversions using a pre-calibrated lookup table or perform conversion computations according to a predetermined conversion formula.

As described hereinabove, the phase shift circuit 24 is provided in a serially connected loop of—the vibration detection sensor 16—DC blocking capacitor—amplifier 22—vibrator 14—object 8—vibration detection sensor—, and has a function for changing the frequency and shifting the phase difference to zero when a phase difference occurs between the input waveform to the vibrator 14 and the output waveform from the vibration detection sensor 16. As shown in FIG. 9, it is preferable for the transfer-characteristic reference curve showing the amplitude characteristic and the phase characteristic with respect to the frequency of the phase shift circuit 24 to have maximum amplitude and invert a phase at the operating frequency $f_r$. With the operating frequency $f_r$ as the resonance frequency, a circuit having this characteristic can be obtained by designing a band-pass filter where the amplitude gain is a maximum at the resonance frequency. More specifically, this circuit can be configured in hardware by the placement of electronic components or by implementing digital filter characteristics in software.

To describe the function of the phase shift circuit 24, a comparison can be made with a vibration system loop that does not include the phase shift circuit. Namely, the vibration system loop, formed from—the vibration detection sensor—DC blocking capacitor—amplifier—vibrator—object—vibration detection sensor—, forms a self oscillation circuit. Even when the hardness sensor 12 (vibrator 14+vibration detection sensor 16) is not in contact with the object 8, the self oscillation circuit is consisted with the space between the vibrator 14 and the vibration detection sensor 16 assuming the role as an object. And the overall system oscillates in a stable manner at some resonance frequency. Next, when the hardness sensor 12 (vibrator 14+vibration detection sensor 16) is in contact with the real object, the oscillation state of the overall system changes due to the influence of the mechanical vibration system for the real object. Namely, due to the magnitude of the spring constant expressing the hardness that describes the vibration system for the real object, a phase difference occurs or a change in frequency occurs. There are already many examples of the prior art of attempts to detect the frequency change and measure the hardness of objects. However, changes in the resonance frequency are usually extremely small so that precise detection is difficult. Moreover, there are few satisfactory measurement means for phase difference detection. The phase shift circuit 24 uses a transfer characteristic reference curve that expresses the amplitude characteristic and the phase characteristic with respect to frequency as described in FIG. 9, converts the change in phase to a change in frequency, and converts the difficulty to measure phase difference detection to an easiness to measure frequency measurement.

The effect will be described when the phase shift circuit 24 is provided in a serially connected loop of—the vibration detection sensor 16—DC blocking capacitor—amplifier 22—vibrator 14—object 8—vibration detection sensor 16—. When the phase shift circuit 24 is connected in the self oscillating loop that includes a real object, which has a mechanical vibration system, and an electrical oscillation circuit, the overall system operates so that the self oscillation is sustained under a condition which is called 'velocity resonance'. 'Velocity resonance' refers a resonance having a maximum amplitude and a phase of zero at the resonance frequency. Namely, when the hardness sensor 12 (vibrator 14+vibration detection sensor 16) is not in contact with the real object 8, the operating point of the phase shift circuit 24 is determined so that the operation is stable at a frequency where the phase difference becomes zero between the input waveform to the vibrator 14 and the output waveform from the vibration detection sensor 16 with the space between the vibrator 14 and the vibration detection sensor 16 assuming the role as an object. This state is shown in FIG. 9 by frequency $f_1$ and phase $\theta_1$.

Next, when the hardness sensor 12 (vibrator 14+vibration detection sensor 16) is in contact with the real object 8, a phase difference occurs between the input waveform to the vibrator 14 and the output waveform from the vibration detection sensor 16 due to the mechanical vibration system for the real object 8, namely, the magnitude of the spring constant expressing the hardness. Now, if the phase difference of only $\Delta\theta$ occurs due to the hardness of the object 8, the operating point of the phase shift circuit 24 shifts so that the self oscillation is sustained by 'the velocity resonance', namely, so that the phase difference $\Delta\theta$ is compensated and the phase difference of the overall system becomes zero. As described by FIG. 9, the operating point of phase $\theta_1$ and frequency $f_1$ shifts to the operating point of phase $\theta_1+\Delta\theta$ and frequency $f_1+\Delta f$, and with the phase difference of the overall system here at zero, 'the velocity resonance' is sustained and stable.

Namely, by connecting the phase shift circuit 24 in series within the loop formed—the vibration detection sensor 16—DC blocking capacitor—amplifier 22—vibrator 14—object 8—vibration detection sensor 16—, a phase difference $\Delta\theta$ compensation necessary for sustaining 'the velocity resonance' is performed. Simultaneously, the magnitude of the phase difference $\Delta\theta$ for which compensation was performed can be converted to the frequency deviation $\Delta f$. The frequency deviation $\Delta f$ that is obtained here is not the amount of change in the resonance frequency as in the prior art but the result of converting the amount of phase change into an amount of frequency change according to the transfer characteristic reference curve for the phase shift circuit 24. Thus, the conversion coefficient $\Delta f/\Delta\theta$ can have an arbitrary magnitude depending on the design of the reference transfer characteristic curve for the phase shift circuit 24. Namely, a small phase difference can be converted to a large frequency deviation or an excessively large phase difference can be converted to a frequency deviation having an appropriate magnitude.

The frequency deviation obtained in this manner can be measured by an appropriate frequency counter and then converted to a hardness value on the basis of a predetermined frequency deviation versus hardness calibration relationship.

SUMMARY OF THE INVENTION

The hardness sensor 12 has many peaks in its frequency versus amplitude characteristic and frequency versus phase characteristic. Therefore, as described hereinabove, when forming the loop,—the vibration detection sensor 16—DC blocking capacitor—amplifier 22—phase shift circuit 24—vibrator 14—object 8—vibration detection sensor 16—, depending a selection of the operating frequency $f_f$ for the phase shift circuit 24, various responses of the vibration loop enable at various frequencies. The operating frequency $f_f$ for the phase shift circuit 24 is set for an appropriate conversion coefficient $\Delta f/\Delta\theta$ using when the phase difference $\Delta\theta$ that occurs when the hardness sensor 12 is in contact with the object 8 is converted to the frequency deviation $\Delta f$. So, the operating frequency $f_f$ for the phase shift circuit 24 is set from the shape of the transfer characteristic reference curve and the operating frequency $f_1$ when the hardness sensor 12 is not in contact with the real object 8. Therefore, to precisely measure the hardness of the object 8, it is necessary to select one from among various peaks in its frequency versus amplitude characteristic and frequency versus phase characteristic of the hardness sensor 12 to be used in hardness measurement. And depending to the operating frequency $f_1$, it is necessary to set the shape of the transfer characteristic reference curve for the phase shift circuit 24 and to set the operating frequency $f_f$.

Hitherto, the selection of a peak to be used in hardness measurement from among the various peaks of the hardness sensor depended on know-how. Therefore, in hardness measurements using a phase shift circuit, setting of the conditions for measuring the hardness of the object 8 at high precision required considerable time and effort.

It is an advantage of the present invention to provide an operating frequency selection method and an operating frequency selection apparatus to facilitate the selection of an operating frequency in a hardness measurement system for measuring the hardness of an object using a phase shift circuit. It is another object to provide a hardness measurement system for performing hardness measurements by selecting the operating frequency for use in the hardness measurements. The means hereinafter contribute to implementing at least one of these advantages.

An operating frequency selection method for the hardness measurement system relating to the present invention is a method for selecting an operating frequency in the hardness measurement system for measuring the hardness of an object from a change in frequency that occurs according to the hardness of the object and comprising a hardness sensor having a vibrator for applying vibrations to the object and a vibration detection sensor for detecting signals reflected from the object, and a phase shift circuit, which is connected in series with an amplifier to the hardness sensor, for changing the frequency and shifting the phase difference thereof to zero when a phase difference occurs between an input waveform to the vibrator and an output waveform from the vibration detection sensor, and the method comprises a peak detection step for detecting multiple peaks and distinguishing each peak in amplitude characteristic with respect to frequency or phase characteristic with respect to frequency, under a condition that the hardness sensor is a free end state and not in contact with a test piece; a free end characteristic acquisition step for measuring and storing in a memory at least one of frequency, phase, or amplitude at each peak position for the distinguished peaks; a contact characteristic acquisition step for measuring and storing in a memory at least one of frequency, phase, or amplitude that changes for each peak of the distinguished peaks when the hardness sensor is placed into contact with the test piece; a peak selection step for selecting a peak for use in hardness measurement on the basis of at least one of frequency change, phase change, or amplitude change between the free end characteristic and the contact characteristic for each peak of the distinguished peaks; and an operating frequency setting step for setting the frequency of the free end state of the selected peak as the operating frequency of the hardness sensor and setting a frequency separated by an arbitrary frequency width from the operating frequency of the hardness sensor as the operating frequency of the phase shift circuit.

According to the aforementioned configuration, multiple peaks in the amplitude characteristic with respect to frequency or phase characteristic with respect to frequency of the hardness sensor are detected, the frequency change, phase change, and amplitude change are obtained for each peak when the hardness sensor is not in contact with and is in contact with the test piece, and a peak is selected for use in hardness measurement accordingly. The peak selection criterion can be set to match the purpose of the measurement. Regarding the frequency change, phase change, and amplitude change, one of three may be obtained as the basis of the selection criterion, or two of three may be obtained, such as the frequency change and the phase change, as the basis of the selection criterion, or all three of the frequency change, phase change, and amplitude change may be combined as the basis of the selection criterion. For example, for the criterion, an appropriate magnitude of phase change may be used or a peak having the largest phase change may be selected, or a peak may be selected among a frequency range that is convenient for measurement. In this manner, the selection of the operating frequency for hardness measurement systems can be further facilitated.

Furthermore, an operating frequency selection method for the hardness measurement system relating to the present invention is a method for selecting an operating frequency in the hardness measurement system for measuring the hardness of an object from a change in frequency that occurs according to the hardness of the object and comprising a hardness sensor having a vibrator for applying vibrations to the object and a vibration detection sensor for detecting signals reflected from the object, and a phase shift circuit, which is connected in series with an amplifier to the hardness sensor, for changing the frequency and shifting the phase difference thereof to zero when a phase difference occurs between an input waveform to the vibrator and an output waveform from the vibration detection sensor, and the method comprises a peak detection step for detecting multiple peaks and distinguishing each peak in amplitude characteristic with respect to frequency or phase characteristic with respect to frequency under a condition that the hardness sensor is in a free end state and not in contact with a test piece; a free end characteristic acquisition step for measuring and storing in a memory at least one of frequency, phase, or amplitude at each peak position for the distinguished peaks; a first characteristic acquisition step for measuring and storing in a memory at least one of frequency, phase, or amplitude that changes for each peak of the distinguished peaks when the hardness sensor is placed into contact with a soft first test piece; a second characteristic acquisition step for measuring and storing in a memory at least one of frequency, phase, or amplitude that changes for each peak of the distinguished peaks when the hardness sensor is placed into contact with a second test piece, which is harder than the first test piece; a peak selection step for selecting a peak for use in hardness measurement on the basis of at least one of frequency change, phase change, or amplitude change between the free end characteristic and the first characteristic for each peak of the distinguished peaks and at least one of frequency change, phase change, or amplitude change between the free end characteristic and the second characteristic for each peak of the distinguished peaks; and an operating frequency setting step for setting the frequency of the free end state of the selected peak as the operating frequency of the hardness sensor and setting a frequency separated by an arbitrary frequency width from the operating frequency of the hardness sensor as the operating frequency of the phase shift circuit.

According to the aforementioned configuration, multiple peaks in the amplitude characteristic with respect to frequency or phase characteristic with respect to frequency of the hardness sensor are detected. Then, a soft test piece and a hard test piece are prepared and the differences for the two types of test pieces in the frequency change, phase change, and amplitude characteristic for each peak when the hardness sensor is in contact with and is not in contact with the test pieces are obtained. Then, based on the results, a peak is selected for use in the hardness measurement. Therefore, a peak can be selected to correspond favorably within the range of hardness and softness of the two types of test pieces so that the selection of the operating frequency for the hardness measurement system can be further facilitated. Regarding the frequency change, phase change, and amplitude change, one of three may be used as the basis of the selection criterion, or two of three may be selected, such as the frequency change and the phase change, as the basis of the selection criterion, or all three of the frequency change, phase change, and amplitude change may be combined as the basis of the selection criterion.

Furthermore, the peak selection step compares the direction of the frequency change and the direction of the phase change between the free end characteristic and the first characteristic and the direction of the frequency change and the direction of the phase change between the free end characteristic and the second characteristic and selects a peak from among the candidate peaks changing in mutually opposite directions.

According to the aforementioned configuration, a peak which having the larger change in phase within the range of hardness and softness of two test pieces can be selected, and the selection of the operating frequency in the hardness measurement system can be further facilitated.

Furthermore, it is preferable for the peak selection step to select from among candidate peaks where the first characteristic change compared to the free end characteristic change in a decreasing direction for both frequency and phase and the second characteristic change compared to the free end characteristic change in an increasing direction for both frequency and phase.

Generally, the frequency deviates toward the lower frequency and the phase decreases as a substance becomes softer and the frequency deviates toward the higher frequency and the phase increases as a substance becomes harder. According to the aforementioned configuration, a peak can be selected along a response characteristic with respect to general substances. Of course, as the function of the phase shift circuit is the conversion of phase and frequency, and even if the selected peak does not have this property, a peak can be selected on the basis of another selection criterion, such as better sensitivity or more stable oscillation.

Furthermore, it is preferable for the peak selection step to select a peak having a large change amount from among the candidate peaks. According to the aforementioned configuration, a peak that increases the sensitivity with respect to hardness can be selected.

Furthermore, it is preferable for the peak detection step to further include a frequency limiting step for narrowing down a peak in an arbitrary frequency range from among multiple peaks. If the shape and material of the hardness sensors are the same, the response characteristics with respect to a test piece are substantially identical. For example, there are instances where the specifications of the hardness sensor are already set and it is already known in which frequency range the suitable peak for the hardness measurement exists. According to the aforementioned configuration, by narrow determining the frequency range in the peak detection step, the selection of the operating frequency in the hardness measurement system can be further facilitated.

Furthermore, it is preferable for the peak detection step to further include a Q value limiting step for narrowing down a peak having a Q value that is less than or equal to an arbitrary Q value from among multiple peaks.

The Q value is a characteristic value expressing the sharpness of a peak. For example, in the amplitude versus frequency characteristic, the half-width of the peak, namely, the frequency width where the amplitude is half with respect to the maximum amplitude of the peak can be used. Generally, a peak with a large Q value indicates a stable vibration, for example, and the changes in the vibration state are small even when contact is made with an object. The primary natural frequency of a vibrating body typically has a high Q value. In a vibration loop system using a phase shift circuit, a larger shift in phase when contact is made with an object is desirable. Furthermore, the shift in phase is compensated by the phase shift circuit so that a higher stability is desirable for the vibrations. According to the aforementioned configuration, since a peak having an appropriately Q value, namely an appropriately stable vibration is selected, the selection of the operating frequency for the hardness measurement system can be further facilitated.

Furthermore, it is preferable for the peak detection step to further include a phase change rate limiting step for narrowing down a peak that has a phase change rate less than or equal to an arbitrary value at the peak position from among multiple peaks.

If the phase changes rapidly in a peak, the sensitivity can be increased. However, on the other hand, the vibrations are liable to be unstable. According to the aforementioned configuration, a peak can be selected to ensure appropriately stable vibrations.

Furthermore, it is preferable for the operating frequency setting step to set an arbitrary frequency width according to the Q value of the phase shift circuit.

As described with FIG. 9, the conversion coefficient $\Delta f/\Delta \theta$ for converting the phase difference $\Delta \theta$ in the phase shift circuit 24 to the frequency deviation $\Delta f$ is determined by the shape of the transfer characteristic reference curve for the phase shift circuit 24, namely, by the Q value, and the frequency width between the operating frequency $f_f$ having maximum amplitude for the phase shift circuit 24 and the operating frequency $f_1$ when contact is not made with the object 8. According to the aforementioned configuration, since the frequency width between $f_f$ and $f_1$ is set according to the Q value of the phase shift circuit, an appropriate conversion coefficient $\Delta f/\Delta \theta$ can be obtained.

Furthermore, the operating frequency selection apparatus for the hardness measurement system relating to the present invention for measuring the hardness of an object from a change in frequency that occurs according to the hardness of the object and comprising a hardness sensor having a vibrator for applying vibrations to the object and a vibration detection sensor for detecting signals reflected from the object, and a phase shift circuit, which is connected in series with an amplifier to the hardness sensor, for changing the frequency and shifting the phase difference thereof to zero when a phase difference occurs between an input waveform to the vibrator and an output waveform from the vibration detection sensor, comprises peak detection section for detecting multiple peaks and distinguishing each peak in amplitude characteristic with respect to frequency or phase characteristic with respect to frequency under a condition that the hardness sensor is in a free end state and not in contact with a test piece; free end characteristic acquisition section for measuring and storing in a memory frequency and phase for each peak of the distinguished peaks; contact characteristic acquisition section for measuring and storing in a memory frequency and phase that change for each peak of the distinguished peaks when the hardness sensor is placed into contact with the test piece; peak selection section for selecting a peak for use in hardness measurement on the basis of frequency change and phase change between the free end characteristic and the contact characteristic for each peak of the distinguished peaks; and operating frequency setting section for setting the frequency of the free end state of the selected peak as the operating frequency of the hardness sensor and setting a frequency separated by an arbitrary frequency width from the operating frequency of the hardness sensor as the operating frequency of the phase shift circuit.

Furthermore, the apparatus for selecting an operating frequency for the hardness measurement system relating to the present invention for measuring the hardness of an object from a change in frequency that occurs according to the hardness of the object and comprising a hardness sensor having a vibrator for applying vibrations to the object and a vibration detection sensor for detecting signals reflected from the object, and a phase shift circuit, which is connected in series with an amplifier to the hardness sensor, for changing the frequency and shifting the phase difference thereof to zero when a phase difference occurs between an input waveform to the vibrator and an output waveform from the vibration detection sensor, comprises peak detection section for detecting multiple peaks and distinguishing each peak in amplitude characteristic with respect to frequency or phase characteristic with respect to frequency under a condition that the hardness sensor is in a free end state and not in contact with a test piece; free end characteristic acquisition section for measuring and storing in a memory frequency and phase for each peak of the distinguished peaks; first characteristic acquisition section for measuring and storing in a memory frequency and phase that change for each peak of the distinguished peaks when the hardness sensor is placed into contact with a soft first test piece; second characteristic acquisition section for measuring and storing in a memory frequency and phase that change for each peak of the distinguished peaks when the hardness sensor is placed into contact with a second test piece, which is harder than the first test piece; and peak selection section for selecting a peak for use in hardness measurement on the basis of frequency change and phase change between the free end characteristic and the first characteristic for each peak of the distinguished peaks and frequency change and phase change between the free end characteristic and the second characteristic for each peak of the distinguished peaks; and setting the frequency of the free end state of the selected peak as the operating frequency of the hardness sensor.

Furthermore, it is preferable for the peak selection section to compare the direction of the frequency change and the direction of the phase change between the free end characteristic and the first characteristic and the direction of the frequency change and the direction of the phase change between the free end characteristic and the second characteristic, and select a peak from among candidate peaks mutually changing in opposite directions.

Furthermore, it is preferable for the peak selection section to select from among candidate peaks, in which the first characteristic change compared to the free end characteristic change in a decreasing direction for both frequency and phase and the second characteristic change compared to the free end characteristic change in an increasing direction for both frequency and phase.

Furthermore, it is preferable for the peak selection section to select a peak having a large change amount from among the candidate peaks.

Furthermore, it is preferable for the peak detection section to further include frequency limiting section for narrowing down a peak in an arbitrary frequency range from among multiple peaks.

Furthermore, it is preferable for the peak detection section to further include Q value limiting section for narrowing down a peak having a Q value that is less than or equal to an arbitrary Q value from among multiple peaks.

Furthermore, it is preferable for the peak detection section to further include phase change rate limiting section for narrowing down a peak that has a phase change rate less than or equal to an arbitrary value at the peak position from among multiple peaks.

Furthermore, the hardness measurement system relating to the present invention for measuring the hardness of an object using a hardness sensor comprising a vibrator for applying vibrations to the object and a vibration detection sensor for detecting signals reflected from the object, comprises a first circuit loop, which is an open loop with the sensor amplifier circuit part that the hardness sensor connecting the amplifier in series, that operates in a state where a sweeping signal with changing frequency is input from an external source, multiple peaks appearing in amplitude characteristic with respect to frequency or phase characteristic with respect to frequency are compared to a predetermined criterion and a peak for use in hardness measurement is selected, a selected frequency corresponding to the selected peak is input by a sensor amplifier circuit part , and a selected phase difference corresponding to the selected frequency is output; a second circuit loop, which is a closed loop and in which the phase shift circuit is connected between the input terminal and the output terminal of the sensor amplifier circuit part to close the loop to form a self oscillating loop, for sustaining self oscillation by changing the frequency and shifting the phase difference thereof to zero by the phase shift circuit when a phase difference occurs between an input waveform to and an output waveform from the sensor amplifier circuit part; switching section for switching a circuit loop, which includes the sensor amplifier circuit part, from an operating state under the selected frequency and selected phase difference in the first circuit loop to an operating state where the selected phase difference across both terminals of the sensor amplifier circuit part in the second circuit loop is compensated for by the phase shift circuit and the self oscillation is sustained under the selected frequency; and a frequency deviation output section for outputting a frequency deviation that changed from the selected frequency and compensated a phase difference component based on hardness by the phase shift circuit so that the selected phase difference maintained across both terminals of the sensor amplifier circuit part, where the phase difference component is the phase difference across both terminals of the sensor amplifier circuit part that changes further from the selected phase difference according to the hardness of the object when the hardness sensor is placed in contact with the object after the switching a circuit loop.

According to the aforementioned configuration, a peak is selected for use in the hardness measurement in the first circuit loop, and in this state, the switching section switch to the second circuit loop, which the phase shift circuit is connected, that enters an operating state sustaining the self oscillation under the operating state with the selected frequency and selected phase difference of the first circuit loop by function of the phase shift circuit. Therefore, since the self oscillation can be sustained for the selected peak for hardness measurement, it is not necessary to again set the values for the phase shift circuit to sustain the self oscillation for the peak for hardness measurement and the subsequent hardness measurement is facilitated.

Furthermore, it is preferable for the phase shift circuit in the hardness measurement system relating to the present invention to include a phase locked circuit, in which a phase detector, a voltage controlled oscillator, and a divider are connected in a loop configuration, for locking an oscillation state so that the phase difference between two input of the phase detector is zero where the output of the sensor amplifier circuit part having the selected phase difference and the output of the divider are input to the phase detector, and a compensation signal output section for performing compensation computations on data corresponding to the selected phase difference for the real time detailed data from the divider and accordingly outputting a phase difference compensation signal that compensates the amount of the selected phase difference for one period of the output signal from the sensor amplifier circuit part. And the phase difference compensation signal may provide to the sensor amplifier circuit part as a input signal of the sensor amplifier circuit part.

The phase shift circuit includes a phase locked circuit so that real time detailed data of the locked oscillation state appears on the divider. A compensated data is generated by subtracting the data corresponding to the selected phase difference from the data of the divider, and a phase difference compensation signal is generated accordingly. Therefore, the phase difference compensation signal can be generated without having to vary the value of complex circuit components, such as resistors, capacitors, and inductors.

Furthermore, it is preferable in the hardness measurement system relating to the present invention to include a converter for converting the output of the sensor amplifier circuit part into a digital signal and supplying to the phase shift circuit, and for the compensation signal output section of the phase shift circuit operating from digital signals to further include a divider counter for counting data signals of the voltage controlled oscillator; a full adder circuit for adding data, that compensates for the selected phase difference and has the same number of bits as the number of bits of divider counter, to the divider counter data; and a waveform generator for generating a sine wave signal from data from the full adder circuit. And the generated sine wave signal may provide to the sensor amplifier circuit part as the phase difference compensated signal.

Since the circuit for generating the phase difference compensation signal performs digital signal processing, the circuit configuration can be simplified.

As described hereinabove, according to the operating frequency selection method for the hardness measurement system and the operating frequency selection apparatus for the hardness measurement system relating to the present invention, the selection of the operating frequency can be further facilitated for the hardness measurement system for measuring the hardness of an object using the phase shift circuit. Furthermore, according to the hardness measurement system relating to the present invention, hardness measurements can be facilitated by sustaining the self oscillation in the peak to be used in the hardness measurement.

BRIEF DESCRIPTION OF THE DRAWINGS

FIG. 5 compares the changes in the frequency and phase for the hardness sensor by the four types from type 1 to type 4 in the embodiment relating to the present invention.

FIG. 6 shows one example of a criterion for selecting the peak in the embodiment of the present invention.

DETAILED DESCRIPTION OF THE PREFERRED EMBODIMENTS

Figure 8:
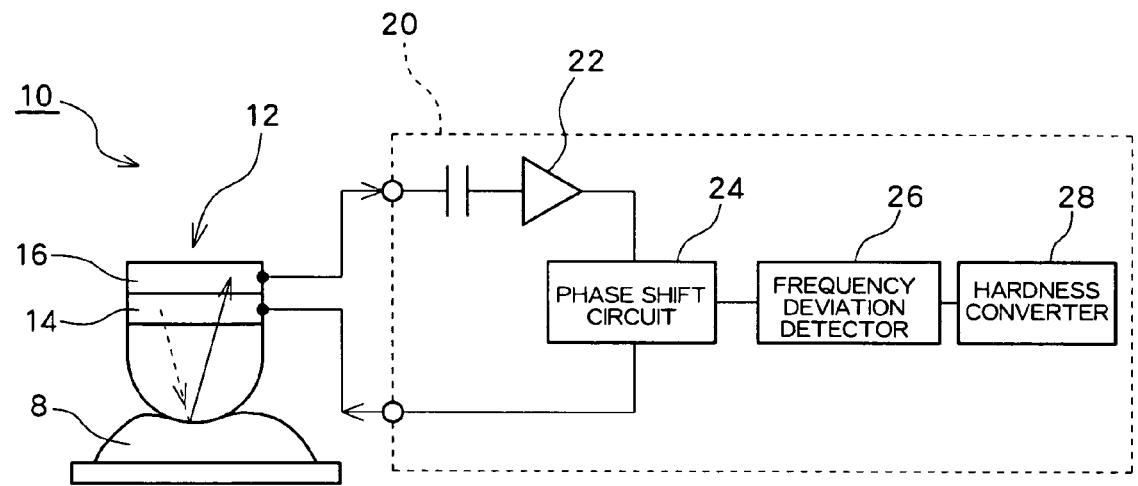
FIG. 8 shows an example of a hardness measurement system using a phase shift circuit in the prior art.

Embodiments relating to the present invention will be described hereinafter. Applicable hardness measurement systems measure the hardness of an object using a phase shift circuit as in the hardness measurement system illustrated by FIG. 8 and FIG. 9. Any object that can be applied with vibrations and have the reflected signals to be detected can be used. For example, the object may be living tissue, such as skin tissue, or an internal organ tissue, such as the liver at a laparotomy, or any other substance, such as a soft gel or a hard solid body.

Furthermore, a hardness sensor in which are stacked two piezoelectric elements, one as a vibrator and the other as a vibration detection sensor, is described hereinafter as the hardness sensor for the operating frequency selection for the hardness measurement system. However, any other configuration that allows vibrations to be input and response signals to be detected from the object may be used for the hardness sensor. For example, the hardness sensor may use one piezoelectric element, where one of two piezoelectric surfaces is grounded and an electrode pattern is provided on the other surface having an outer ring electrode and a central disc electrode. In this case, in response to an AC signal that is input by the outer ring electrode, the peripheral part of the piezoelectric element vibrates to function as a vibrator and the central part of the piezoelectric element functions as a vibration detection sensor with the AC signal corresponding to the detected vibration appearing at the central disc electrode. Furthermore, the vibrator and the vibration detection sensor may be implemented separately and this grouped device may be called the hardness sensor. Moreover, an appropriate contact ball or contact protruding bar may be provided between the hardness sensor and the object.

Figure 1:
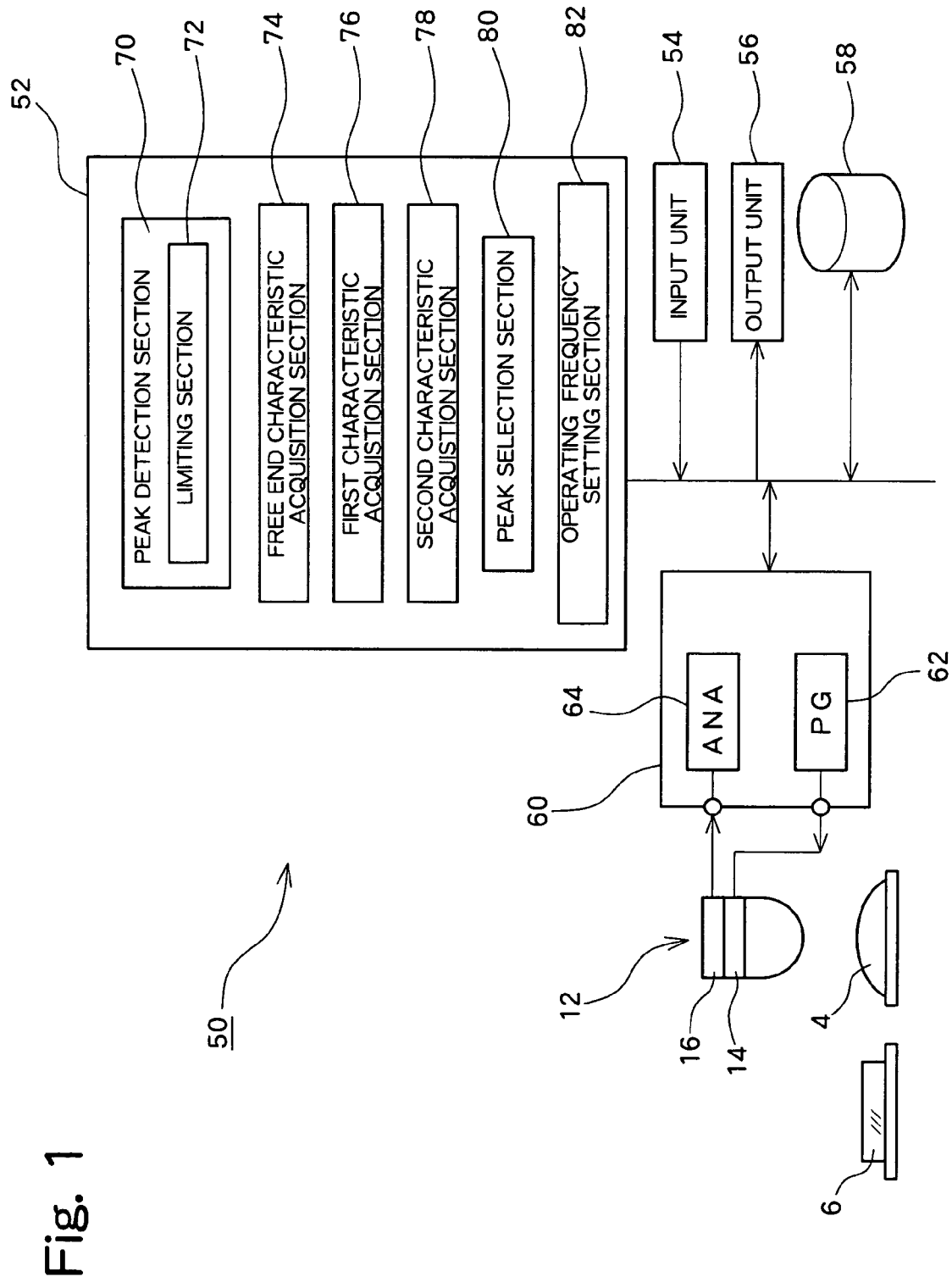
FIG. 1 is a block diagram of an operating frequency selection apparatus of a hardness measurement system in an embodiment relating to the present invention.

FIG. 1 is a block diagram of an operating frequency selection apparatus 50 of a hardness measurement system. The operating frequency selection apparatus 50 of the hardness measurement system (hereinafter referred to as the operating frequency selection apparatus 50) includes a CPU 52, an input unit 54, such as a keyboard, an output unit 56, such as a display or a plotter, a storage device 58 for storing programs and characteristics, and a network analyzer 60 for acquiring the amplitude versus frequency characteristics and the phase versus frequency characteristics of the hardness sensor 12, all of which are interconnected through an internal bus. The operating frequency selection apparatus 50 can be configured using a dedicated computer with built-in network analyzer functions. Furthermore, the operating frequency selection apparatus 50 can be configured by combining a general computer and a general network analyzer.

In FIG. 1, the hardness sensor 12 has the vibrator 14 for applying vibrations to an object (not shown) and the vibration detection sensor 16 for detecting reflected signals from the object. The hardness sensor 12 has two stacked piezoelectric elements of PZT (lead zirconate titanate), one of which is the vibrator 14 and the other is the vibration detection sensor 16. In-the operation for the operating frequency selection apparatus 50, the hardness sensor 12 contacts two test pieces 4, 6 that have been prepared in advance and the amplitude versus frequency characteristic and the phase versus frequency characteristic are measured.

One of the test pieces, test piece 4, is soft and may be an elastic body, such as silicon rubber, affixed to a plate. The other test piece, test piece 6, is harder than the first test piece 4 and may be a piece of wood or rigid plastic affixed to a plate. For the first test piece 4 and the second test piece 6, it is preferable to affix materials representing the respective maximum and minimum limits of the hardness range of objects to be handled by the hardness measurement system. The first test piece 4 and the second test piece 6 may be placed into contact with the hardness sensor 12 by automatic operation under control of the CPU 52 using, for example, a conveyance device or by manual operation where an operator interactively communicates with the operating frequency selection apparatus 50. In a simple case, the first test piece 4 may be the palm of the hand or fingertip of an operator and the second test piece 6 may be the surface of a measurement desk where the operator places the hardness sensor 12 into contact with the palm of the hand or the surface of the measurement desk.

The network analyzer 60 is a measuring instrument having functions to measure and acquire the amplitude versus frequency characteristic and the phase versus frequency characteristic for the hardness sensor and includes a PG unit 62 that can change the frequency and perform a sweep output of pulse signals and a ANA unit 64 for receiving signals and analyzing and measuring the amplitude versus frequency characteristic and the phase versus frequency characteristic. An output terminal from the PG unit 62 is connected to the vibrator 14 of the hardness sensor 12 and an input terminal to the ANA unit is connected to the vibration detection sensor 16 of the hardness sensor 12. More specifically, the network analyzer 60 has functions to receive instructions from the CPU 52, sweep and supply pulses in a predetermined frequency range to the vibrator 14, to analyze the signals received from the vibration detection sensor 16, to measure the amplitude versus frequency characteristic and the phase versus frequency characteristic, and to send the measured and acquired data via the internal bus to the CPU 52.

The CPU 52 has functions to provide instructions to the network analyzer 60, to process data sent from the network analyzer 60, and to select an operating frequency for the hardness measurement system. More specifically, the CPU 52 includes a peak detection section 70 for receiving the amplitude versus frequency characteristic in a free state where the hardness sensor 12 is not in contact with the test piece and detecting multiple peaks, a free end characteristic acquisition section 74 for acquiring the frequency and the phase for each peak, a first characteristic acquisition section 76 for acquiring the frequency and the phase for each peak when the hardness sensor 12 contacts the first test piece 4, a second characteristic acquisition section 78 for acquiring the frequency and the phase of each peak when the hardness sensor 12 contacts the second test piece 6, a peak selection section 80 for selecting a peak to be used in the hardness measurement on the basis of the foregoing acquiring data, and an operating frequency setting section 82 for setting the operating frequency for the hardness measurement system based on the selected peak. The peak detection section 70 includes a limiting section 72 to yield a peak of a certain range among multiple peaks and to facilitate subsequent processes. These functions can be implemented in software, namely, by executing a corresponding operating frequency selection program. Furthermore, some of the functions may be implemented in hardware.

Figure 2:
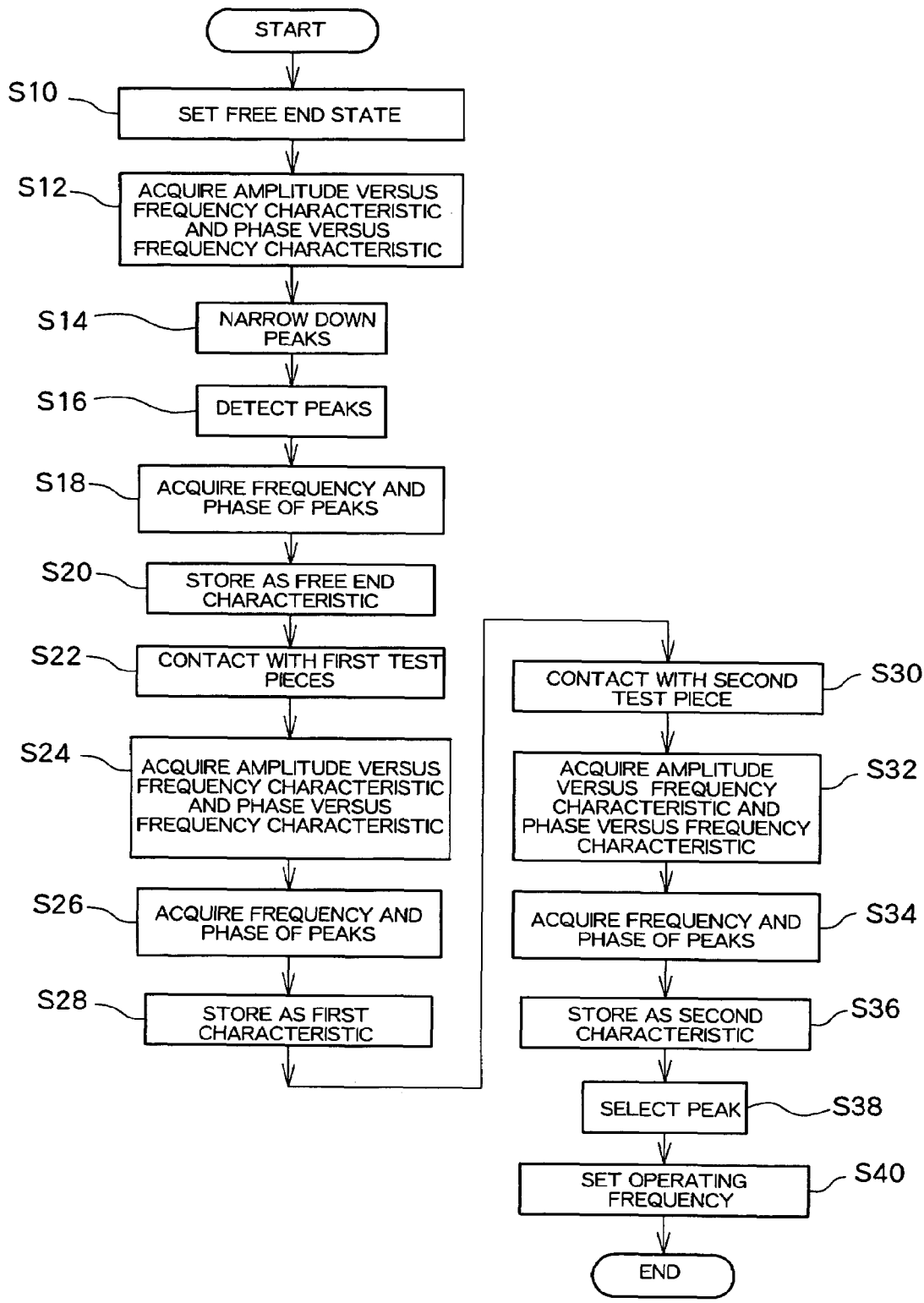
FIG. 2 is a flowchart showing a procedure for operating frequency selection in the embodiment of the present invention.

The action of the operating frequency selection apparatus 50 with the aforementioned configuration will be described, particularly the functions of the CPU 52, by using the flowchart of FIG. 2 that shows a procedure of selecting the operating frequency.

To perform the procedure for selecting the operating frequency, the hardness sensor 12, for which the operating frequency is to be selected, is first connected to the network analyzer 60 using the aforementioned connection method. Next, the corresponding operating frequency selection program is started. Then, according to its instruction, the hardness sensor 12 is set to a free end state (S10). More specifically, the hardness sensor 12 is in a free end state where it does not contact any object. As described above, the hardness sensor 12 may be automatically moved in a direction to separate from the test piece, such as by using a conveyance device, or the operator may communicate with the operating frequency selection apparatus 50 and issue an instruction to "set the free end state" so that the hardness sensor 12 is placed in a free state.

The amplitude versus frequency characteristic and the phase versus frequency characteristic are then-acquired (S12). More specifically, from part of the function of the peak detection section 70 in the CPU 52, an instruction is provided to the network analyzer 60, sweeping pulse signals in a predetermined frequency range are provided to the vibrator 14, a signal is received from the vibration detection sensor 16, and the amplitude versus frequency characteristic and the phase versus frequency characteristic are measured and acquired. The acquired amplitude versus frequency characteristic and the acquired phase versus frequency characteristic are initially stored into the storage device 58.

Figure 3:
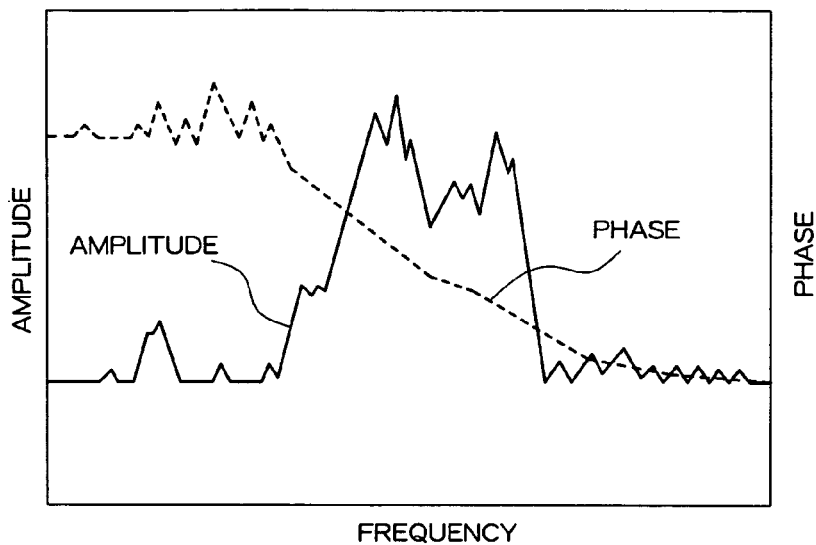
FIG. 3 shows an example of amplitude versus frequency characteristic and phase versus frequency characteristic acquired with a hardness sensor.

FIG. 3 shows an example of the acquired amplitude versus frequency characteristic and the acquired phase versus frequency characteristic. FIG. 3 shows the amplitude versus frequency characteristic and the phase versus frequency characteristic as displayed on one display screen so as to be easily viewed. With the frequency on the abscissa and the amplitude and the phase on the ordinate, the amplitude versus frequency characteristic is shown by a solid line and the phase versus frequency characteristic is shown by a dashed line. The sweeping frequency range can be set to a wide range, for example, 1 kHz to 10 MHz, and the amplitude covers a wide amplitude range in the frequency range and the phase also covers a wide phase range in the frequency range.

Looking at the amplitude versus frequency characteristic in FIG. 3, a considerable number of peaks are found in this frequency range. Similarly, looking at the phase versus frequency characteristic, a considerable number of peaks are clearly found in this frequency range. The function and also advantage of the operating frequency selection apparatus 50 is to select one of these multiple peaks suitable for hardness measurement. The many peaks are detected and subsequent processing may be performed. At the very beginning, it is preferable to detect all the peaks in the amplitude versus frequency characteristic and all the peaks in the phase versus frequency characteristic and then perform subsequent processing. As data and experience are accumulated, the target peak can be narrowed down.

Then, narrow down peaks is performed (S14). More specifically, the function of the limiting section 72 that is included in the peak detection section 70 of the CPU 52 narrows down the multiple peaks to a peak suitable for subsequent processing in accordance with predetermined limiting criteria.

One limiting criterion is to limit the peak to either the amplitude versus frequency characteristic or the phase versus frequency characteristic. For example, the peaks in the amplitude versus frequency characteristic may be the target peaks.

Furthermore, one limiting criterion is to limit the frequency range to a predetermined range and then to a peak in the limited frequency range. For example, while handling a hardness sensor having a certain configuration and certain material, that type of hardness sensor may be found based on experience to have a peak suitable for a hardness measurement near by a certain frequency range. More specifically, if a hardness sensor is configured by stacking piezoelectric elements having a diameter of 10 mm and a thickness of 1 mm and is found to have a peak suitable for hardness measurements near several tens of kHz, it is possible to limit the frequency range to 10 kHz to 100 kHz.

Furthermore, one limiting criterion is to restrict the range of Q values of the peaks. The Q value of a peak is a characteristic value expressing the sharpness of the peak and a half-width of the peak, for example, can be used. If the half-width of the peak is narrow, the vibration represented by the peak is often stable. When contact is made with the test piece, there is little change in frequency and phase so that a sufficient sensitivity cannot be obtained in the hardness measurement. Thus, it is preferable to narrow down the peaks to one having a half-width of the peak greater than or equal to a predetermined value. For example, with Q value =half-width/frequency, the selection can be narrowed down to peaks having a Q value of 1% or more.

Furthermore, one limiting criterion is to restrict the rate of change in phase at the peak position. When a peak having a phase that changes rapidly at the peak frequency is used, a large $\Delta\theta/\Delta$ may be obtained. However, at the same time, the vibration becomes unstable so that the accuracy of the hardness measured value decreases. The rate of change in phase at the frequency of the peak may be narrowed down to a predetermined value or lower. For example, the rate of change in phase in the half-width of the peak can be narrowed down to 45 degrees or less.

Furthermore, one limiting criterion is to eliminate the peaks in a small range where many peaks appear. A range in which many peaks together appear often has multimode vibrations where the vibrations are unstable and unsuitable for hardness measurements. Thus, it is preferable to narrow down the peaks to one where the peaks are not congested. For example, narrowing down to a peak where the number of peaks/bandwidth is less than or equal to a predetermined value. Or, an operator may eliminate a range where peaks are congested and specify a desired range on a screen of amplitude versus frequency characteristic and a screen of phase versus frequency characteristic.

When using these limiting criteria, a suitable material may be added to the hardness sensor and used to improve the rate of change in phase at the peak position or the Q value at the peak. For example, if the peak is at a frequency that is easy to measure but the Q value is too sharp, a viscous material can be added to the contact surface of the hardness sensor to yield a suitable Q value and a suitable phase change. Similarly, if the rate of change in phase is too large also, a suitable material can be added to yield a suitable rate of change in phase.

These limiting criteria may be used individually or in combination. For example, the limiting can be performed so that the Q value of the peak in the amplitude characteristic or the half width/frequency is larger than 1% in the amplitude versus frequency characteristic with the frequency range set to 10 kHz-100 kHz.

Returning back to FIG. 2, peak detection (S16) is performed for the limited ranged. More specifically, from part of the function of the peak detection section 70 in the CPU 52, all peaks in the limited range are detected (S16) using a known peak detection method. For the known peak detection method, maximum value detection, turning point detection in a differential coefficient, and so forth, can be employed.

Then, for each detected peak, the frequency and phase at the peak position are acquired (S18). The acquired frequency and phase of each peak position are stored (S20) as the free end characteristic. More specifically, from a function of the free end characteristic acquisition section 74, the detected peaks are attached with identification keys, such as labels, and using comparison with the amplitude versus frequency characteristic and the phase versus frequency characteristic that were stored in the storage device 58 in step S12, and then the frequency and the phase at the peak position for each peak is acquired and stored in the storage device 58 together with the identification keys distinguishing the peaks. The free end characteristic are a collection of frequency and phase data at the peak position of the peaks.

When the free end characteristic is acquired and stored in this manner, the hardness sensor 12 is next placed in contact (S22) with the first test piece 4. Similar to what was described in S10, the contact may be performed automatically, or manually in an interactive format by an operator, such as "contact the first test piece". When performed manually, the contact may be simply made with the palm of the hand of the operator and handled this palm as the first test piece.

Then, the amplitude versus frequency characteristic and the phase versus frequency characteristic are acquired (S24). More specifically, from part of the function of the first characteristic acquisition section 76, similar to what was described in step S12, an instruction is provided to the network analyzer 60, sweeping pulse signals of a predetermined frequency range are provided to the vibrator 14, signals are received from the vibration detection sensor 16, and their amplitude versus frequency characteristic and the phase versus frequency characteristic are measured and acquired. The acquired amplitude versus frequency characteristic and the phase versus frequency characteristic are initially stored into the storage device 58.

Next, regarding the peaks detected in S16, the frequency and the phase of each peak position are acquired (S26). The acquired frequency and the acquired phase of each peak position are stored (S28) as the first characteristic. More specifically, from part of the function of the first characteristic acquisition section 76, regarding the peaks already attached with identification keys, such as labels, the amplitude versus frequency characteristic and the phase versus frequency characteristic stored in the storage device 58 in step S24 are compared, and the frequency and the phase at the peak positions are acquired and stored into the storage device 58 together with the identification keys distinguishing the peaks. The first characteristic is a collection of frequency and phase data at the peak position of the peaks.

When the first characteristic is acquired and stored in this manner, the hardness sensor 12 is next placed in contact (S30) with the second test piece 6. Similar to what was described in S10 and S22, the contact may be performed automatically, or manually in an interactive format by an operator, such as "contact the second test piece". When performed manually, the contact may be simply made with the surface of the measurement desk and handled this desk as the second test piece.

Then, the amplitude versus frequency characteristic and the phase versus frequency characteristic are acquired (S32). More specifically, from part of the function of the second characteristic acquisition section 78, similar to what was described in steps S12 and S24, an instruction is provided to the network analyzer 60, sweeping pulse signals of a predetermined frequency range are provided to the vibrator 14, signals are received from the vibration detection sensor 16, and their amplitude versus frequency characteristic and the phase versus frequency characteristic are measured and acquired. The acquired amplitude versus frequency characteristic and the phase versus frequency characteristic are initially stored into the storage device 58.

Next, regarding the peaks detected in S16, the frequency and phase of each peak position are acquired (S34). The acquired frequency and the acquired phase of each peak position are stored (S36) as the second characteristic. More specifically, from part of the function of the second characteristic acquisition section 78, regarding the peaks already attached with identification keys, such as labels, the amplitude versus frequency characteristic and the phase versus frequency characteristic stored in the storage device 58 in step S32 are compared, and the frequency and the phase at the peak positions are acquired and stored into the storage device 58 together with the identification keys distinguishing the peaks. The second characteristic is a collection of frequency and phase data at the peak position of the peaks.

When the first characteristic and the second characteristic are acquired and stored in this manner, peak selection suitable for hardness measurement is performed (S38) accordingly. More specifically, from the function of the peak selection section 80, the data for the peaks of the free end characteristic, the first characteristic, and the second characteristic undergo a selection process based on a predetermined criterion, and one peak suitable for hardness measurement is selected.

Figure 4:
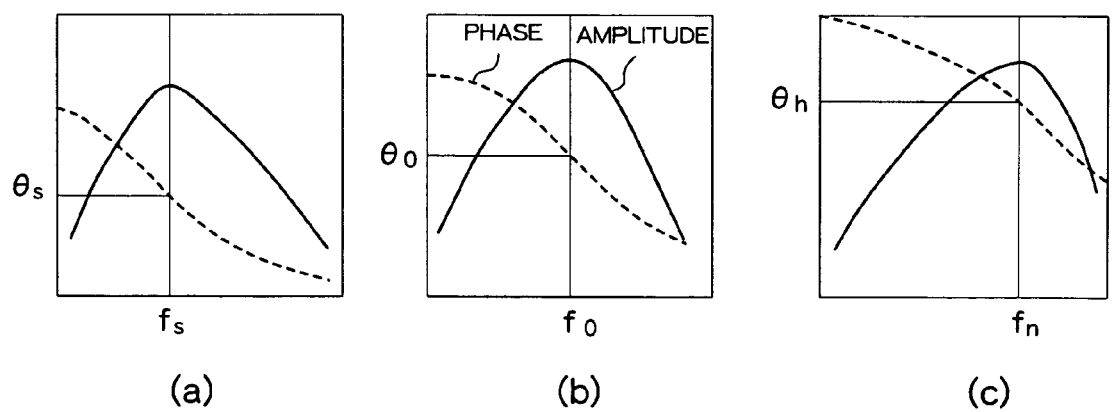
FIG. 4 compares the free end characteristic, the first characteristic, and the second characteristic at a certain peak to illustrate peak selection in the embodiment relating to the present invention.

To describe peak selection, the free end characteristic, the first characteristic, and the second characteristic for a peak are shown in a row in FIG. 4. The amplitude versus frequency characteristic and the phase versus frequency characteristic in the free end state are shown enlarged in FIG. 4(b). The amplitude versus frequency characteristic and the phase versus frequency characteristic when contact is made with the first test piece 4 are shown to the left in FIG. 4(a) and the amplitude versus frequency characteristic and the phase versus frequency characteristic when contact is made with the second test piece 6 are shown to the right in FIG. 4(c). They are all shown with the frequency on the abscissa and the amplitude and the phase on the ordinate, and with the amplitude versus frequency characteristic shown by a solid line and the phase versus frequency characteristic shown by a dashed line.

In the example of FIG. 4, the frequency $f_0$ and phase $\theta_0$ at the peak position in the free end state change so that the frequency shifts to a lower frequency of $f_s$ and the phase changes to a small value of $\theta_s$ when contact is made with the first test piece 4 and the frequency shifts to a higher frequency of $f_h$ and the phase changes to a large value of $\theta_h$ when contact is made with the second test piece 6. Looking at the change in frequency and the change in phase, the frequency and the phase decrease when contact is made with the first test piece 4 from the free end state, and the frequency and the phase increase when contact is made with the second test piece 6 from the free end state.

FIG. 5 classifies the types of changes in the frequency and the phase and shows type 1 to type 4 in a row. It should be noted that in a typical vibrating body, the change in frequency and the change in amplitude are often in opposite directions. In this sort of instance, instead of classifying the type according to the change in frequency and the change in phase, the type may be classified according to the change in amplitude and phase. In this manner, there are four possible combinations and each peak should be classified into one of these four types. However, the mechanism of how a specific peak belongs to which specific type is still currently not clear. Therefore, when determining the suitability of the hardness sensor to the hardness measurement, the hardness sensor is placed in contact with a test piece and it is preferable to consider not only the change in phase at that time but also the change in frequency or the change in amplitude. The following describes an instance where the frequency change and the phase change are considered.

When the frequency change and the phase change are considered, the peak selection criterion can be set using these four types. Normally, it can be used as a criterion for selecting a peak having the characteristic shown in FIG. 6. Namely, the selection criteria for the peak suitable for hardness measurement is that the change from the free end state when contact is made with the soft first test piece 4 is type 4 and the change from the free end state when contact is made with the hard second test piece 6 is type 1. A peak satisfying the selection criteria of FIG. 6 has a characteristic where the frequency and the phase decrease when contact is made with a soft object and increase when contact is made with a hard object. Since the directions of the changes are opposite in this manner, the change in phase difference can be enlarged and useful.

Furthermore, this sort of vibration system having a peak has a trend similar to that of vibration system having single degree of freedom. Therefore, using this sort of peak, the hardness measurement of objects matches the single degree of freedom vibration system model so that a measurement is performed similar to an ordinary physical phenomenon. Incidentally, the example of FIG. 4 shows peaks matching the selection criterion of FIG. 6 so that these peaks in FIG. 4 can be selected as peaks suitable for hardness measurements.

Furthermore, another peak selection criterion is the selection of a peak that has a larger change in phase difference among the types of FIG. 6. According to this criterion, the sensitivity of the hardness detection can be further improved.

It is possible to select another peak selection criterion is the selection of a peak suitable for hardness measurements that the change when contacting the soft first test piece 4 from the free end state is type 2 and the change when contacting the hard second test piece 6 from the free end state is type 3. Or, a peak where the change when contacting the soft first test piece 4 from the free end state is type 3 and the change when contacting the hard second test piece 6 from the free end state is type 2 may be selected as the peak suitable for hardness measurements. Although this case differs from the single degree of freedom vibration model, the change in phase difference can be enlarged and useful since the directions of change are in opposite directions.

Furthermore, another peak selection criterion is possible to select a selection criterion based on another criterion, such as higher sensitivity or more stable oscillation, and not adhering to the type classifications of FIG. 5.

These peak selection criteria may be combined provided they do not contradict each other. For example, when multiple peaks are selected even if using the selection criterion of FIG. 6, the one having the maximum phase difference can be selected. In this manner, the predetermined peak selection criterion should apply to characteristic change of the peaks and the peak selection is performed to select one peak matching the peak selection criterion from multiple peaks.

Figure 7:
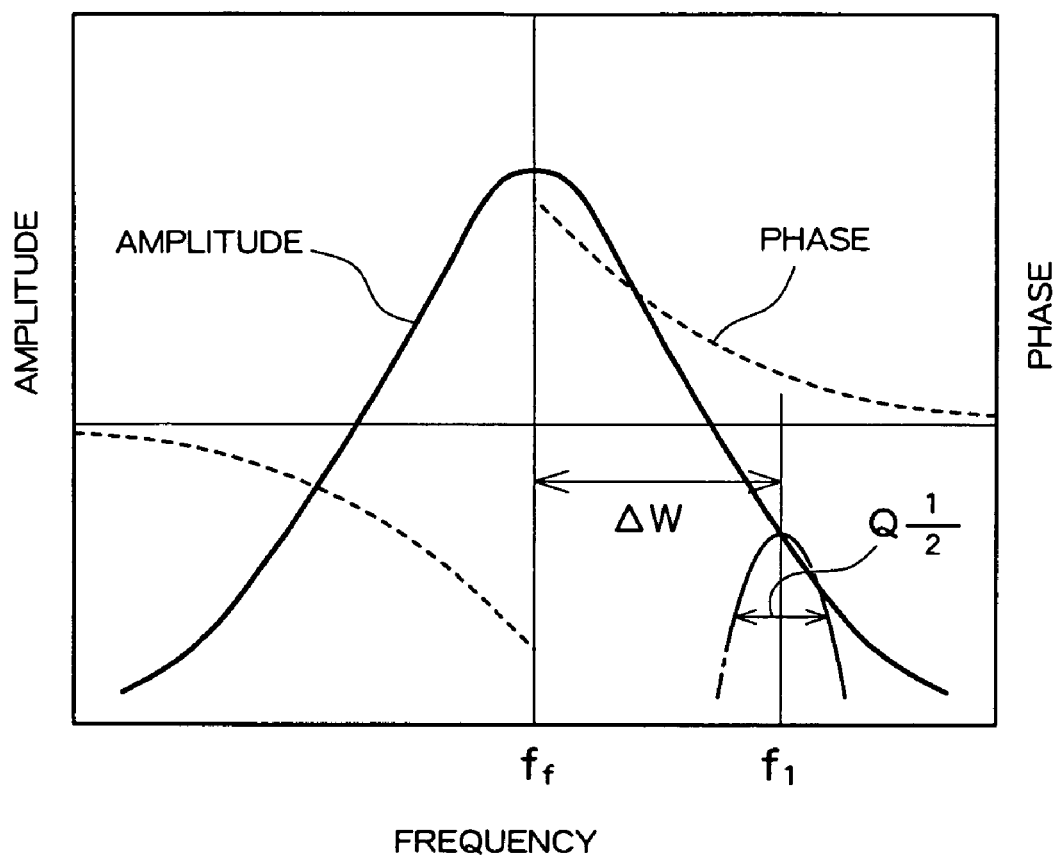
FIG. 7 illustrates the setting of the operating frequency for the hardness sensor and a phase shift circuit in the embodiment relating to the present invention.

When one peak is selected as being suitable for hardness measurements, from a function of the operating frequency setting section 82, the setting of the operating frequency is performed (S40). First, the frequency in the free end state of the selected peak becomes the operating frequency $f_1$ for the hardness sensor. Then, as shown in FIG. 7, the operating frequency $f_f$ of the phase shift circuit 24 is set to be separated from $f_1$ by a predetermined frequency width $\Delta W$. The predetermined frequency width $\Delta W$ can be set according to the Q value of the phase shift circuit 24, namely, the sharpness of the peak of the amplitude versus frequency characteristic. Namely, when the Q value of the phase shift circuit 24 is large, the peak is sharp, and the change in $\Delta\theta/\Delta f$ is large, $\Delta W$ may be set large and phase difference compensation may be performed where $\Delta\theta/\Delta f$ is small far from $f_f$. Conversely, when the peak is gradual and the change in $\Delta\theta/\Delta f$ is small, $\Delta W$ may be set small and phase difference compensation may be performed where $\Delta\theta/\Delta f$ is large near $f_f$.

Hereinabove, each step in the operating frequency selection was described as being performed by executing an operating frequency selection program in the operating frequency selection apparatus 50 that includes a computer. In another method without using a computer, these steps can also be executed by a dedicated hardware device centering on the functions of the network analyzer. Furthermore, the operating frequency selection can also be performed by an operator operating an analyzer, such as a general network analyzer, and sequentially performing the steps of FIG. 2.

Next, regarding the process after the peak to be used in the hardness measurement has been selected as described hereinabove, a preferred hardness measurement system will be described. For the hardness measurement system described with FIG. 8, by using the hardness sensor 12, which has the vibrator 14 for applying a vibration to the object 8 and the vibration detection sensor 16 for detecting the signal that is reflected from the object 8, a circuit loop connecting the hardness sensor 12, the amplifier 22, and the phase shift circuit 24 in series can be used. Since this circuit loop is a closed loop, self oscillation can be initiated depending on the characteristics of the hardness sensor 12, the amplifier 22, and the phase shift circuit 24. In this case, it is necessary to set the circuit loop characteristic so that the self oscillation occurs near the selected frequency and the selected phase difference for the peak to be used in the hardness measurement, and more particularly it is necessary to set the characteristic of the phase shift circuit 24. The hardness measurement system to be described hereinafter is intended to facilitate the setting where self oscillation occurs under the selected frequency and the selected phase difference for the peak to be used in the hardness measurement.

Figure 9:
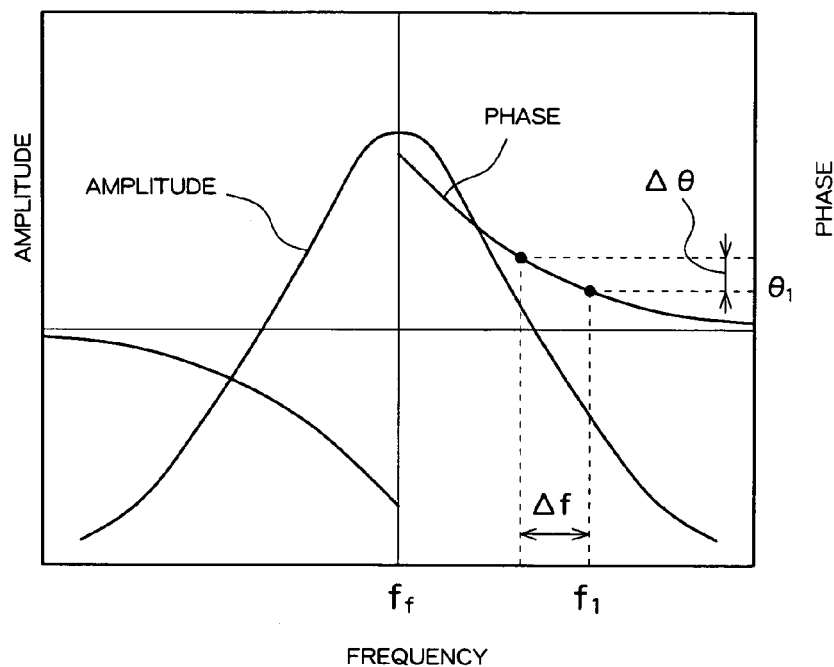
FIG. 9 shows an example of a transfer characteristic reference curve of a phase shift circuit in the prior art.
Figure 10:
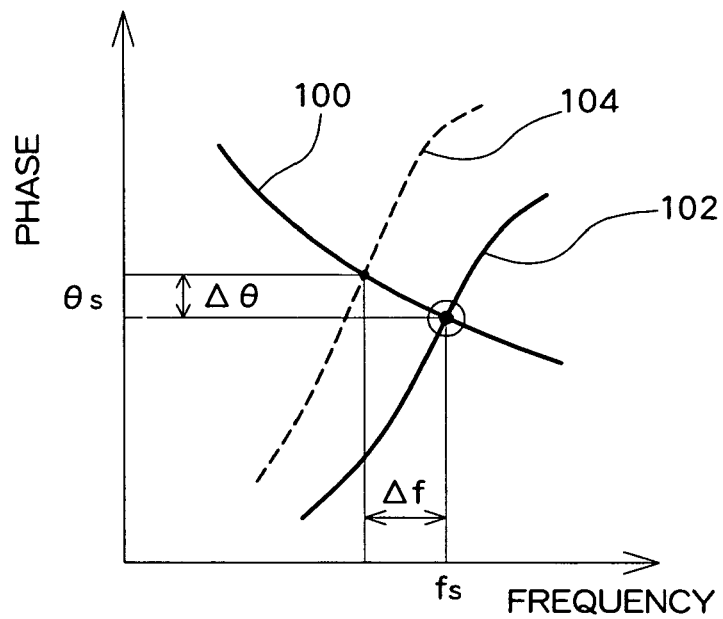
FIG. 10 illustrates a hardness measurement when using a phase shift circuit that has the transfer characteristic reference curve in the prior art.

A phase shift circuit can be used having the transfer reference characteristic curve shown in FIG. 9 with an amplitude peak at frequency $f_f$. As described with FIG. 7, the operating frequency $f_f$ of the phase shift circuit is set on the basis of the operating frequency $f_1$ of the hardness sensor 12, namely, the selected frequency to be used in the hardness measurement. The phase shift circuit having this transfer characteristic reference curve can be obtained by combining circuit components, such as resistors, capacitors, and inductors, and setting their values appropriately. FIG. 10 illustrates an aspect of the hardness measurement when the phase shift circuit having this transfer characteristic reference curve is used.

With the phase on the ordinate and the frequency on the abscissa in FIG. 10, a phase curve 100 of the transfer characteristic reference curve for the phase shift circuit in FIG. 9 is shown. Furthermore, the phase versus frequency characteristic of the hardness sensor 12 when the hardness sensor 12 is not in contact with the object 8 is shown by a solid line 102 and the phase versus frequency characteristic of the hardness sensor 12 plus the object 8 when the hardness sensor 12 is in contact with the object 8 is shown by a dashed line 104. Then, as described hereinabove, when a peak is selected for the hardness measurement in accordance with a predetermined criterion, the selected frequency $f_s$ and the selected phase difference $\theta_s$ are specified for use in the actual hardness measurement in the neighborhood of the selected peak. And the characteristic of the phase shift circuit is set so as to pass the positions of the selected frequency $f_s$ and the selected phase difference $\theta_s$ of the solid line 102. When the characteristic of the phase shift circuit is set in this manner, the closed loop,— the hardness sensor—amplifier—phase shift circuit—, can self oscillate at the conditions of the selected frequency $f_s$ and the selected phase difference $\theta_s$. When the hardness sensor 12 contacts the object 8 in this state, the oscillation state of the closed loop changes. And the oscillation state position moves to the intersection of the phase curve 100 of the phase shift circuit and the dashed line 104 which indicates the phase versus frequency characteristic of the hardness sensor 12 plus the object 8 when the hardness sensor 12 is in contact with the object 8 as shown in FIG. 10. Namely, a phase difference of $\Delta\theta$ and a frequency deviation of $\Delta f$ are created according to the hardness of the object 8. Since this change depends on the hardness of the object 8, the hardness can be obtained from the detected frequency deviation $\Delta f$.

In this manner, the hardness of an object can be obtained by using a phase shift circuit having the reference transfer characteristic curve described in FIG. 9. However, even if the selected frequency $f_s$ and the selected phase difference $\theta_s$ are selected for use in the hardness measurement, it is necessary to vary the various values of the many circuit components to precisely set the phase shift circuit so that the oscillation state passes through that point. If the values are not set precisely, the self oscillation of the closed loop will not occur at the selected frequency $f_s$ and the selected phase difference $\theta_s$ and the accuracy of the hardness measurement decreases.

Figure 11:
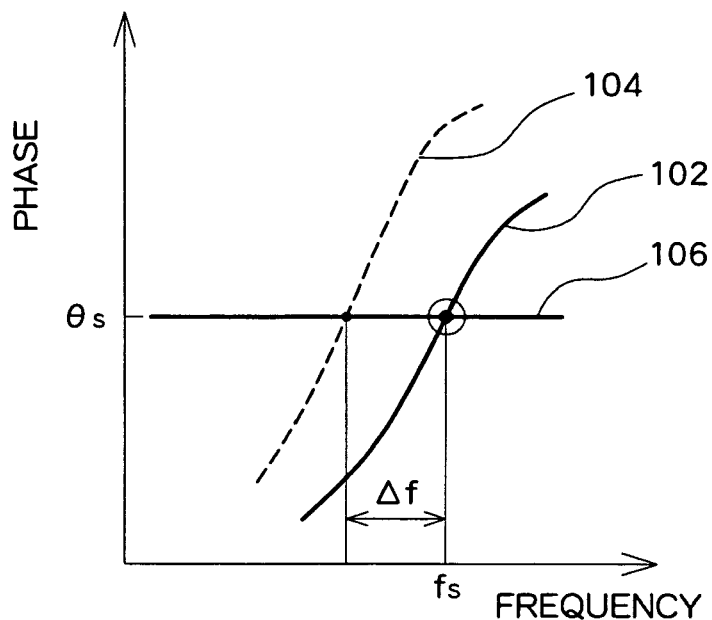
FIG. 11 shows a phase curve for the phase shift circuit in the hardness measurement system of the embodiment of the present invention.

The hardness measurement system to be described hereinafter easily maintains the self oscillation of the closed loop at the selected frequency $f_s$ and the selected phase difference $\theta_s$. The principle of the system will be described first. This new hardness measurement system has a different characteristic for the phase shift circuit than the one described in FIG. 9. FIG. 11 shows an aspect of the phase curve 106 for the new phase shift circuit. Namely, the phase shift circuit has a characteristic to constantly maintain the selected phase difference $\theta_s$ in the closed loop and detects the hardness of the object 8 through the frequency deviation $\Delta f$, which is the change in frequency at the intersection of the solid line 102, which is the characteristic of hardness sensor 12 when the hardness sensor 12 is not in contact with the object 8, and the dashed line 104, which is the characteristic of the hardness sensor 12 plus the object 8 when they are in contact. The phase shift circuit having the effect of FIG. 11 requires a configuration to constantly maintain the phase difference between the input side and the output side of the hardness sensor at the selected phase difference $\theta_s$. However, compared to setting the transfer characteristic reference curve shown in FIG. 9 to a desirable characteristic, a configuration having this function can be easily implemented using the circuit techniques to be described hereinafter.

By using this phase shift circuit, self oscillation is performed at the selected frequency and the selected phase difference for the peak to be used in the hardness measurement and the hardness measurement can be easily performed. Namely, when a signal is input from an external source by the hardness sensor and the amplifier in the open loop and the signal is chosen for the selected frequency $f_s$ for the hardness measurement, the operation starts and the resulting phase difference between the input side and the output side of the hardness sensor and the amplifier corresponds to the selected phase difference $\theta_s$. The operation is continued in this state and then the phase shift circuit is connected to form a closed loop. If the switching from the open loop to the closed loop is quickly performed by an electronic switch, due to the vibration sustaining power of the open loop, switching to the closed loop can be accomplished before the vibrations dampen. So the vibration state at the selected frequency $f_s$ and the selected phase difference $\theta_s$ continues even in the closed loop. At this time, the phase shift circuit should be configured to generate a signal to be able to compensate the selected phase difference in the signal at the output side of the hardness sensor plus the amplifier, and should be configured that the generated signal is supplied to the input side of the hardness sensor plus the amplifier, and then close the loop. This enables the self oscillation to continue so that the phase difference between the input side and the output side of the hardness sensor is constantly maintained at the selected phase difference $\theta_s$.

Figure 12:
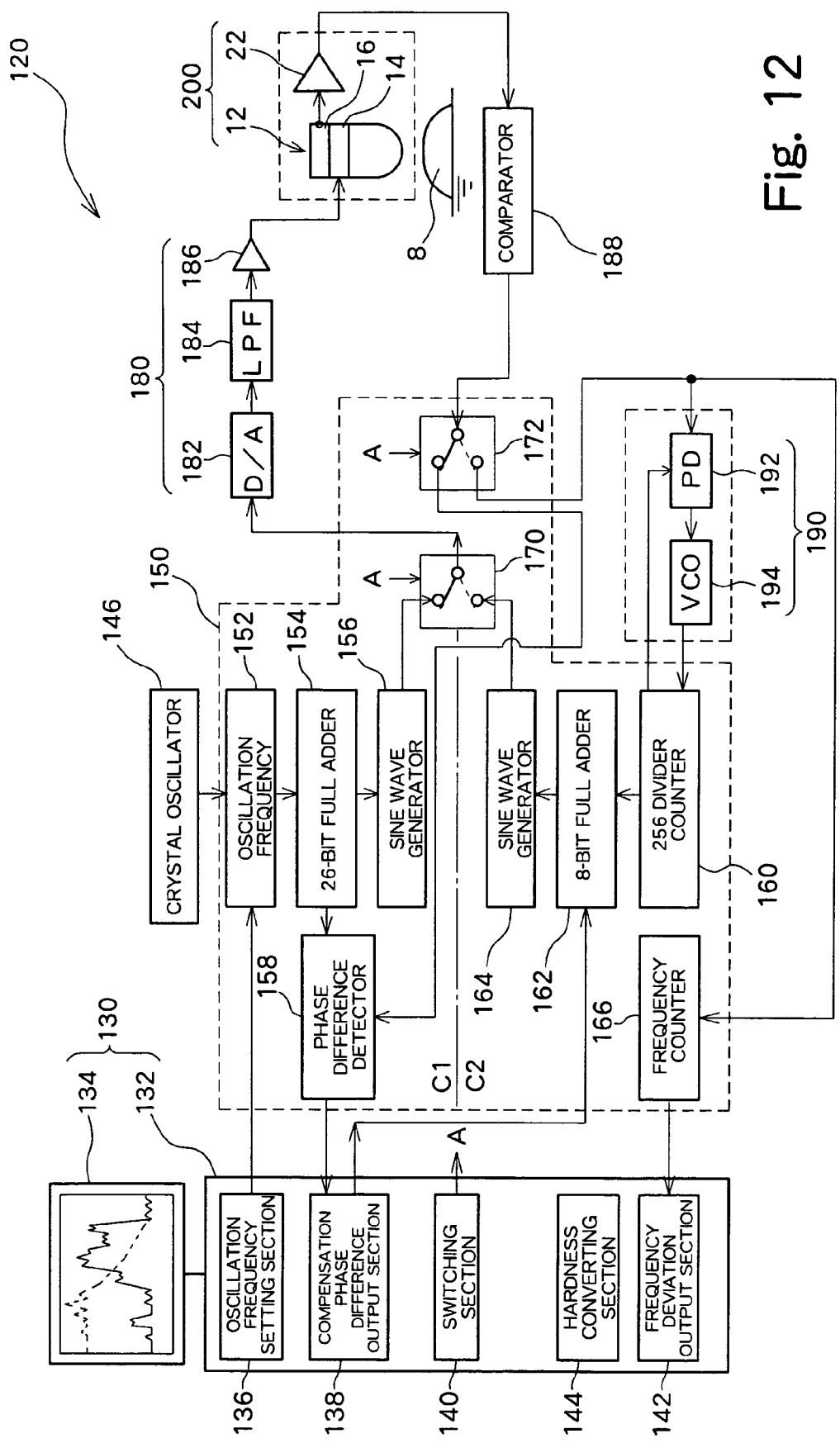
FIG. 12 is a block diagram showing a configuration of the hardness measurement system in the embodiment of the present invention.

Using a new phase shift circuit, a hardness measurement system that facilitates a setting where self oscillation occurs under a fixed frequency and a fixed phase difference selected as a peak to be used in the hardness measurement will be detailed hereinafter. FIG. 12 is a block diagram showing the configuration of a hardness measurement system 120. The hardness measurement system 120 includes a hardness measurement computer 130 for controlling the operation of the overall system, a crystal oscillator 146, a PLA (Programmable Logic Array) 150 that integrates digital circuits, a conversion circuit 180 for converting data from the PLA 150 to a sine waveform, a sensor amplifier circuit part 200 that connects in series the hardness sensor 12 and an amplifier 22 and inputs the sine waveform from the conversion circuit 180, a comparator 188 for digitizing an output signal from the sensor amplifier circuit part 200, and a PLL (Phase Locked Loop) circuit 190.

The PLA 150 includes an open loop digital circuit C1, a closed loop digital circuit C2, and switching circuits 170, 172 for switching the open loop circuit and the closed loop circuit.

The digital circuit C1 of the PLA 150 includes a oscillation frequency setting circuit 152 for synthesizing a signal of a predetermined frequency by digitally processing the master vibration from the crystal oscillator 146, a 26-bit full adder circuit 154, and a sine wave generator 156. The digital circuit C1 of the PLA 150 further includes a phase difference detector 158 for detecting a selected phase difference $\theta_s$, which is the phase difference between the input terminal and the output terminal of the sensor amplifier circuit part 200 under the selected frequency $f_s$, which was selected for use in the hardness measurement. The setting of the frequency setting circuit 152 is performed under control of the hardness measurement computer 130 and the data of the selected phase difference $\theta_s$, which was detected by the phase difference detector 158, is stored into the hardness measurement computer 130.

The digital circuit C2 of the PLA 150 includes a 256 divider counter 160, an 8-bit full adder circuit 162 for adding the data of the 256 divider counter 160 and the data that compensates for the selected phase difference $\theta_s$, and a sine wave generator 164 for generating sine wave data based on a output of the 8-bit full adder circuit 162. Further included is a frequency counter 166 for counting the frequency in the closed circuit loop. The data of the frequency counter 166, when the hardness sensor 12 is not in contact with an object 8 and when it is in contact with the object 8, is respectively received by the hardness measurement computer 130 and the hardness is converted from the frequency deviation between these two frequencies.

The hardness measurement computer 130 includes a controller 132 and a monitor unit 134. The controller 132 includes a CPU and memory and further includes an oscillation frequency setting section 136 for setting the frequency for, the frequency setting circuit 152 of the digital circuit C1, a compensation phase difference output section 138 for receiving and storing the selected phase difference $\theta_s$ that is detected by the digital circuit C1 and outputting it to the 8-bit full adder circuit 162 of the digital circuit C2, a switching section 140 for switching the switching circuits 170, 172, a frequency deviation output section 142 for obtaining the frequency deviation, and a hardness converting section 144 for converting the frequency deviation to a hardness in accordance with a predetermined conversion method.

The hardness measurement system 120 activates the switching circuits 170, 172 due to the function of the switching section 140 in the controller 132 of the hardness measurement computer 130 and switches between the open loop circuit and the closed loop circuit. Hereinafter, their configurations will be described with the open loop circuit referred to as the first circuit loop and the closed loop circuit referred to as the second circuit loop.

Figure 13:
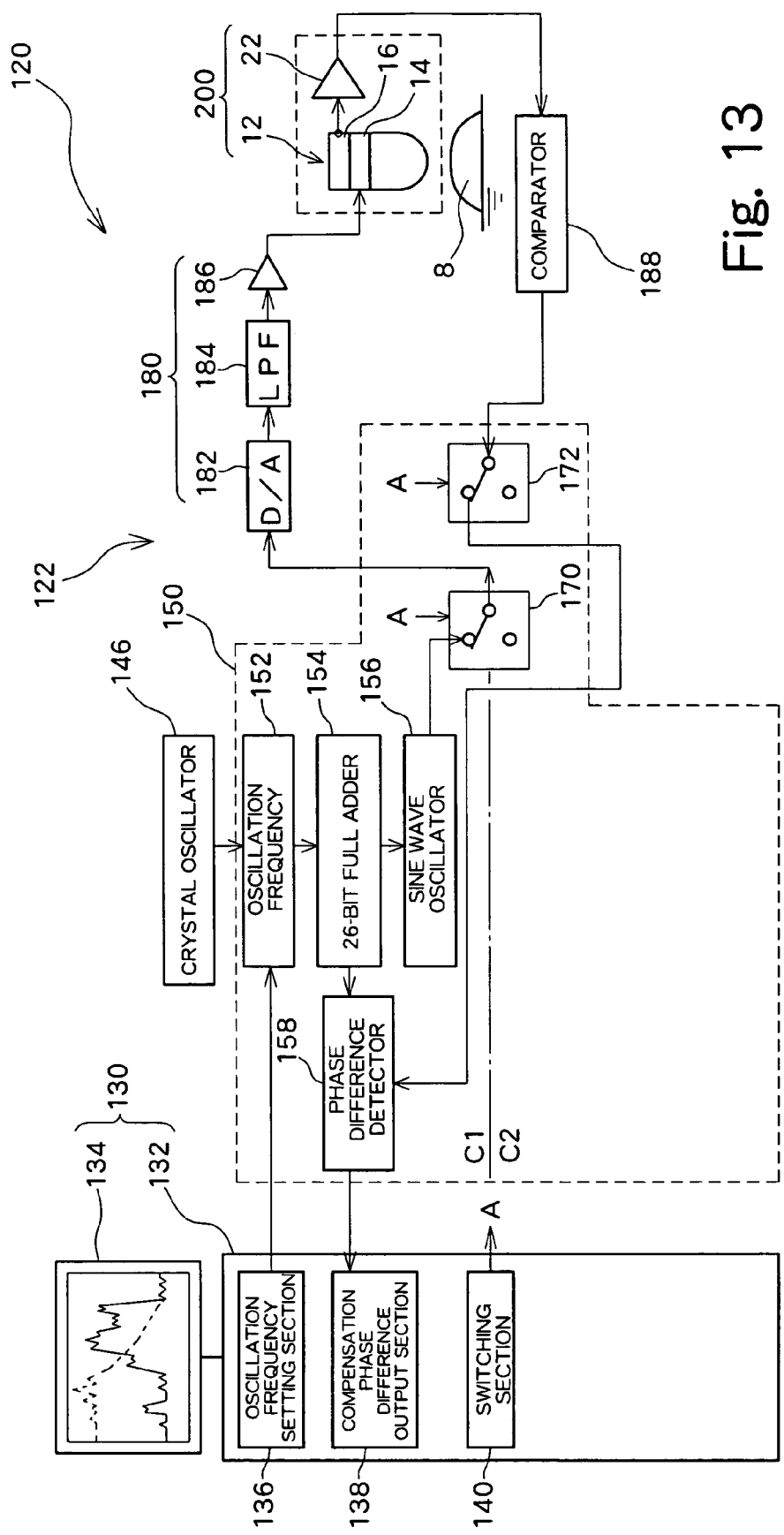
FIG. 13 is a block diagram showing a configuration relating to a first circuit loop in the hardness measurement system in the embodiment of the present invention.

FIG. 13 is a block diagram showing a configuration relating to a first circuit loop 122. The first circuit loop 122 is configured by the switching circuits 170, 172 switching to the upper side of the diagram in FIG. 13 with a signal A from the switching section 140 in the controller 132. The first circuit loop 122 is used to execute functions for selecting a peak to be used in the hardness measurement, having the sensor amplifier circuit part 200 input a selected frequency, and storing the phase difference between the input terminal and the output terminal of the sensor amplifier circuit part 200 as the selected phase difference $\theta_s$.

The first circuit loop 122 has an open loop configuration from the crystal oscillator 146—oscillation frequency setting circuit 152—26-bit full adder circuit 154—sine wave generator 156—(switching circuit 170)—a D/A converter 182—a low-pass filter 184—a buffer circuit 186—vibrator 14—(open space)—vibration detection sensor 16—amplifier 22—comparator 188—(switching circuit 172).

In the first circuit loop 122, the part, including the crystal oscillator 146, the oscillation frequency setting circuit 152, the 26-bit full adder circuit 154, and the sine wave oscillator 156, functions using the master vibration of the crystal oscillator 146 to synthesize a signal at a frequency set at the oscillation frequency setting circuit 152 for output as sine wave data at a resolution of 26 bits. This function can be configured using a known digital circuit technology called DDS (Direct Digital Synthesis). For example, in the oscillation frequency setting section 136 in the controller 132, when 100 kHz is set, a process is performed to generate a 100 kHz sine wave signal from the master vibration in the oscillation frequency setting circuit 152, and a 10 μsec duration, which is one period of 100 kHz, is divided into 26 bits, and data for the peak value of the sine wave is set in the 26-bit full adder circuit 154 and then a sine wave data is generated and output. In this manner, the digital data of the sine wave signal at the set frequency is output to the conversion circuit 180 via the switching circuit 170.

Under control of the switching section 140 in the controller 132, the switching circuit 170 has a function to switch the data output to the conversion circuit 180 from either the sine wave generator 156 in the digital circuit C1 or the sine wave generator 164 in the digital circuit C2. The switching circuit 170 can be configured from a latch circuit to latch data from the sine wave generators 156, 164 and a multiplexer circuit to switch the connection of the data lines of multiple bits.

The conversion circuit 180 has functions to convert the output sine wave digital data to an analog signal waveform and supply it to the sensor amplifier circuit part 200 with the noise removed. More specifically, the conversion circuit 180 is configured from the D/A converter 182, the low-pass filter 184 for removing noise, and the buffer circuit 186 described hereinabove.

The sensor amplifier circuit part 200 has the sensor 12 and the amplifier 22 connected in series as described hereinabove. Their configurations are identical to those described in FIG. 8 so that they are designated same reference characters and their descriptions will be omitted.

This completes the basic configuration of the open loop. To detect the phase difference between the input terminal and the output terminal of the sensor amplifier circuit part 200, the output of the amplifier 22 is digitized by the comparator 188 and input via the switching circuit 172 as one signal by the phase difference detector 158 in the digital circuit C1. Data from the 26-bit full adder circuit 154 is input as the other signal by the phase difference detector 158. The phase difference between the input terminal and the output terminal of the sensor amplifier circuit part 200 is detected by comparing these two signals. The phase difference detector 158 can use a known digital circuit for detecting the pulse advance or lag. It should be noted that the switching circuit 172 is identical to the aforementioned switching circuit 170.

To select the peak to be used in the hardness measurement in the first circuit loop 122, an arbitrary frequency sweep range is set at the oscillation frequency setting section 136 in the controller 132. For example, on an input unit, such as a keyboard (not shown) at the hardness measurement computer 130, an operator enters 40 kHz to 170 kHz as an arbitrary frequency sweep range and the data is acquired by the controller 132 to set the sweep mode in the oscillation frequency setting section 136. When the range of 40 kHz to 170 kHz is set for the sweep mode in this manner, a sine wave generation process is constantly performed at the oscillation frequency setting circuit 152 in the digital circuit C1 of the PLA 150 in accordance with predetermined period unit and predetermined frequency unit. If the period unit is 10 msec and the frequency unit is 50 Hz, once a 40.00 kHz sine wave is generated, a 40.05 kHz sine wave is generated after 10 msec and the frequency is increased by 50 Hz every 10 msec until 170 kHz. Once 170 kHz is attained, the frequency returns back to 40 kHz and this process is repeated. Therefore, the sensor amplifier circuit part 200 inputs a repeating sine wave signal sweeping from 40 kHz to 170 kHz.

The phase difference detector 158 detects the phase difference between the input terminal and the output terminal of the sensor amplifier circuit part 200. Thus, if the phase difference and the frequency that is input by the sensor amplifier circuit part 200 are output to the monitor 134, the operator can observe the phase characteristic with respect to frequency of the sensor amplifier circuit part 200. Furthermore, if the signal amplitude gain between the input terminal and the output terminal of the sensor amplifier circuit part 200 is acquired and output to the monitor 134, the amplitude characteristic with respect to frequency and the phase characteristic with respect to frequency illustrated in FIG. 3 can be observed. While observing these characteristics on the monitor 134, a test piece is placed in contact with the hardness sensor 12. And from the changes in the peaks at the time, a peak is narrowed down from the limiting criterion already described and used as the selected peak for use in the hardness measurement. And the neighborhood frequency and the neighborhood phase difference are set respectively to the selected frequency $f_s$ and the selected phase difference $\theta_s$.

As one example, the selected frequency $f_s$ is 100 kHz and the selected phase difference $\theta_s$ is −25° with respect to the input side, namely, a selection is made so that the phase of the output side lags the phase of the input side. When the selected frequency $f_s$ and the selected phase difference $\theta_s$ are set in this manner, the signal input by the sensor amplifier circuit part 200 is continually fixed at the selected frequency $f_s$, or at 100 kHz in the aforementioned example. At this time, the phase difference between the input terminal and the output terminal of the sensor amplifier circuit 200 is the selected phase difference $\theta_s$, namely, −25° in the aforementioned example, and the phase difference is maintained while the signal at the selected frequency $f_s$ of 100 kHz is continually input. Then, the selected phase difference $\theta_s$, namely, the data of −25° in the aforementioned example, is converted to digital data and stored into the compensation phase difference output section 138 in the controller 132. For example, with 360° displayed as 8 bits, −25° is stored as −00001010. This data is then used so that in the next second circuit loop 124, the code for the selected phase difference $\theta_s$ is inverted as data to compensate for the phase difference and the compensation phase difference output section 138 outputs the inverted data for $\theta_s$ as a compensation phase difference. In the aforementioned example, −00001010 is output as the compensation phase difference.

Figure 14:
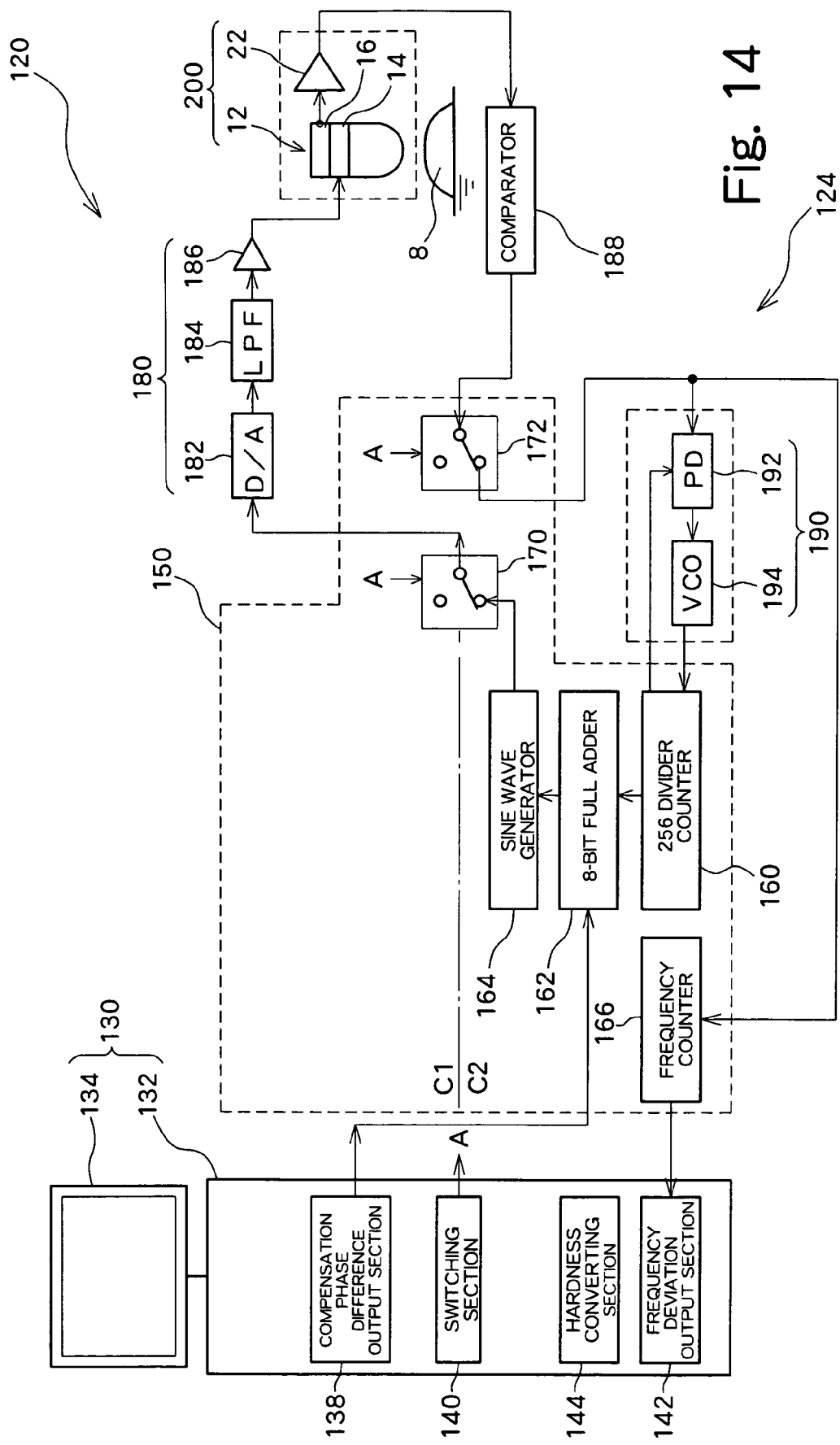
FIG. 14 is a block diagram showing a configuration relating to a second circuit loop in the hardness measurement system in the embodiment of the present invention.

Next, FIG. 14 is a block diagram showing the configuration relating to the second circuit loop 124. The second circuit loop 124 is configured by the switching circuits 170, 172 switching to the lower side of the diagram in FIG. 14 with the signal A from the switching section 140 in the controller 132. Here, the switching circuits 170, 172 are electronically switched by the multiplexer circuit as described hereinabove and the configuration of the first circuit loop can be quickly switched to the configuration of the second circuit loop, foe example in an interval of several tens of nsec. During this interval, the operation of the first circuit loop, namely, the operation for vibrating the vibrator 12 at the selected frequency $f_s$, is not appreciably damped. Therefore, even after switching, the vibration at the selected frequency $f_s$ continues in the second circuit loop 124. In the continuing vibration state after switching in this manner, the second circuit loop 124 is used to execute a function for continuing the self oscillation while in a state where a signal at the selected frequency $f_s$ is input by the sensor amplifier circuit part 200 and the selected phase difference $\theta_s$ occurs between the input terminal and the output terminal of the sensor amplifier circuit 20.

The second circuit loop 124 has a closed loop configuration,—vibrator 14—(open space)—vibration detection sensor 16—amplifier 22—comparator 188—a phase detector 192—a VCO (voltage controlled oscillator) 194—256 divider counter 160—sine wave generator 164—(switching circuit 170)—D/A converter 182—low-pass filter 184—buffer circuit 186—(vibrator 14——). Here, the part from the phase detector 192 to the sine wave generator 164 has the function of a phase shift circuit.

In the second circuit loop 124, the part including the phase detector 192, the VCO 194, and the 256 divider counter 160 is a circuit performing so-called PLL operations. The output of the sensor amplifier circuit part 200 is used for the input signal of one side of the phase detector 192 and the output of the 256 divider counter 160 is used for the input signal of the other side. In this configuration, the phase detector 192 outputs a voltage corresponding to the shift in phase between the two signals, the VCO 194 outputs a signal at a frequency in proportion to the magnitude of the output voltage, and the output is divided by 256 by the 256 divider counter 160 and again returned to the phase detector 192. Therefore, as an overall operation of this circuit, the PLL operation uses this feedback to eliminate the phase difference between the two signals in the phase detector 192, namely, to lock a signal at a frequency having a phase difference of zero.

For example, in the aforementioned example at a selected frequency $f_s$ of 100 kHz, a 25.6 MHz pulse signal is input by the 256 divider counter 160 so that the signal divided by 256 in the 256 divider counter 160 locks at 100 kHz. Therefore, the output data of the 256 divider counter 160 represents the $f_s$=100 kHz signal at full scale of 8-bit. In other words, one period of the selected frequency $f_s$=100 kHz is represented continuously as 8-bit data.

The 8-bit full adder circuit 162 has a function to add a data, that is output from the compensation phase difference output section 138, to the continuous data of the 256 divider counter 160 to compensate for the selected phase difference $\theta_s$. For example, if the data of the 256 divider counter 160 at a certain time is 01000000, the data of the compensation phase difference $\theta_s$ in the aforementioned example is −00001010 and the data to compensate for this is +00001010. Thus, a full 8-bit addition can be performed to yield 01001010. Compared to the data prior to addition, the data after addition has an advanced phase.

The sine wave generator 164 has a function similar to the aforementioned sine wave generator 156 and the peak value data of the sine wave is output in a state where the phase has been advanced in accordance with the output of the 8-bit full adder circuit 162. The digital data of the sine wave signal with compensation for the selected phase difference $\theta_s$ is input by the sensor amplifier circuit part 200 via the switching circuit 170 and the conversion circuit 180. Therefore, the phase difference between the input terminal and the output terminal remains at the selected phase difference $\theta_s$ in the sensor amplifier circuit part 200. However, in the overall second circuit loop 124, this selected phase difference $\theta_s$ is compensated by the phase shift circuit from the aforementioned phase detector 192 to the sine weave generator 164 so that the self oscillation can be continued.

Figure 15:
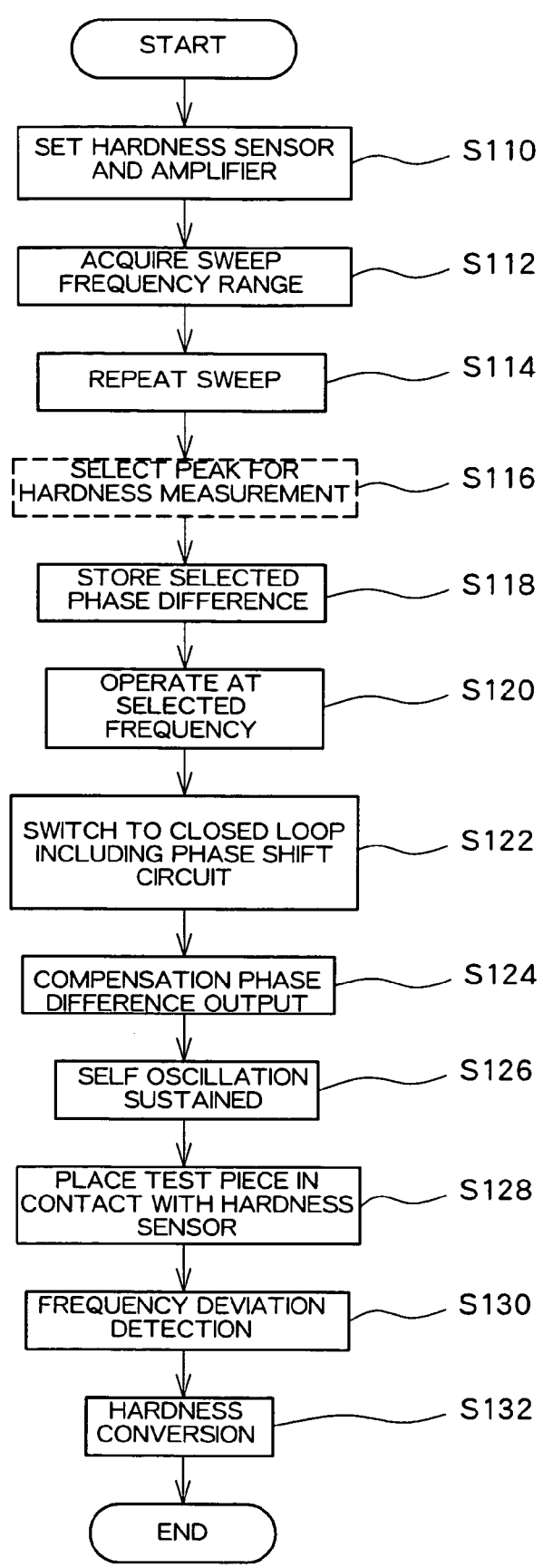
FIG. 15 is a flowchart showing a procedure for measuring the hardness of an object for the hardness measurement system in the embodiment of the present invention.

A procedure to measure the hardness of the object 8 using the hardness measurement system 120 with this configuration will be described using the flowchart of FIG. 15. The procedure is realized from the functions of the oscillation frequency setting section 136, the compensation phase difference output section 138, the switching section 140, the frequency deviation output section 142, and the hardness converting section 144 in the controller 132 of the hardness measurement computer 130. These functions can be implemented in software, and more specifically, by executing a corresponding hardness measurement program. Furthermore, these functions may be configured so that part of each function is implemented in hardware.

First, the system is started up and the hardness measurement program is initiated. At this time, the switching section 140 provides instructions to the switching circuits 170, 172 so that the first circuit loop 122 is selected. The amplifier 22 and the hardness sensor 12 to be used for the hardness measurement are set (S110). As illustrated in FIG. 12, the setting is performed by connecting the hardness sensor 12 and the amplifier 22 in series between the conversion circuit 180 and the comparator 188. The hardness measurement system 120 can be handled as a replaceable unit with the sensor amplifier circuit part 200 having the hardness sensor 12 and the amplifier 22 connected in series. Also, only the hardness sensor 12 may be replaceable, while the amplifier 22 is fixed.

Next, the sweep frequency range is input and its value is acquired (S112). More specifically, from a function of the oscillation frequency setting section 136 in the controller 132, the input data is acquired, such as from an operator keyboard as describe hereinabove, and becomes the set value of the oscillation frequency. In the aforementioned example, a sweep frequency range of 40 kHz to 120 kHz is acquired. If the hardness sensor 12 is already provided, the sweep frequency range can be appropriately set based on experience or prior experiments.

The input signal to the sensor amplifier circuit part 200 is repeatedly swept (S114) in the acquired sweep frequency range. More specifically, this is performed by the functions of the elements from the crystal oscillator 146 to the sine wave generator 156. As described hereinabove, the phase difference between the input terminal and the output terminal of the sensor amplifier circuit part 200 is detected by the phase difference detector 158 and the amplitude characteristic with respect to frequency and the phase characteristic with respect to frequency are displayed on the monitor unit 134. While viewing this screen, the operator selects (S116) and narrows down for a peak to be used in the hardness measurement in accordance with a predetermined criterion. This procedure can be performed as illustrated in FIG. 2. Since this process can be performed by the operator interactively with the hardness measurement computer 130, this procedure is shown by a dashed line in FIG. 15. Of course, the contact with the test piece and the comparison with the predetermined limiting criterion may be automated.

When the peak is selected for hardness measurement, the data for its selected phase difference $\theta_s$ is input and stored (S118) by the compensation phase difference output section 138. In the aforementioned example, the data −00001010 is stored. Furthermore, the sweep frequency is fixed at the selected frequency $f_s$, and in this state, the input to the sensor amplifier circuit part 200 continues and the vibrator 14 continues vibrations (S120) at that frequency. In this operation, the phase difference between the input terminal and the output terminal of the sensor amplifier circuit part 200 remains at the selected phase difference $\theta_s$.

Figure 16:
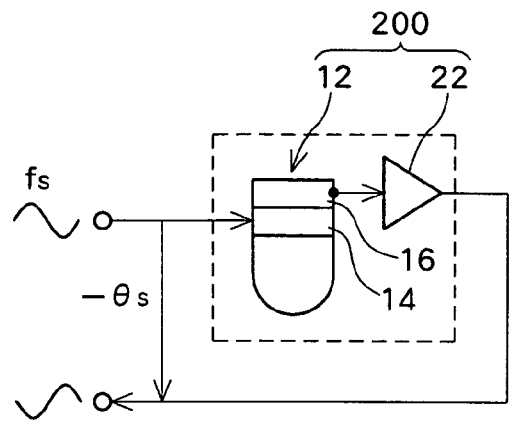
FIG. 16 illustrates a phase difference for the first circuit loop in the hardness measurement system in the embodiment of the present invention.

This aspect is shown in FIG. 16. In this figure, the sensor amplifier circuit part 200 that is configured from the hardness sensor 12 and the amplifier 22 is shown. A signal at the selected frequency $f_s$ is input by the vibrator 14 at the input side of the hardness sensor 12. Then, a signal appearing at the output terminal of the sensor amplifier circuit 200 via the amplifier 22 connected in series to the vibration detection sensor 16 at the output side of the hardness sensor 12 is shifted in phase by the selected phase difference $\theta_s$ with the input signal to the vibrator 14 as reference. This phase shift is caused mainly by the characteristic of the hardness sensor 12. The selected frequency $f_s$ and the selected phase difference $\theta_s$ are favorable for this hardness sensor for measuring the hardness of an object under these conditions and correspond to the central operating condition of the hardness measurement system.

Next, an instruction of the switching section 140 results in switching (S122) to the closed loop including the phase shift circuit. Namely, switching is performed from the configuration of the first circuit loop 122 to the configuration of the second circuit loop 124. As described hereinabove, this switching can be performed in a short time compared to the damping of the vibration of the first circuit loop. From a function of the compensation phase difference output section 138, compensation phase difference data is then output (S124) to compensate for the selected phase difference $\theta_s$. In the aforementioned example, the data +00001010 is output to the 8-bit full adder circuit 162. The order of steps S122 and S124 may be reversed.

As a result, at the condition under which the first circuit loop 122 operates from the switching, namely, as the loop closes at an operating state where the vibrator 14 vibrates at the selected frequency fs and the phase difference between the input terminal and the output terminal of the sensor amplifier circuit part 200 is $\theta_s$, due to the action of the 8-bit full adder 162 and the sine wave generator 164, a sine wave signal having a phase compensating for the selected phase difference $\theta_s$ with reference to the output terminal of the sensor amplifier circuit part 200 is generated and supplied to the input terminal of the sensor amplifier circuit part 200. In the aforementioned example, a sine wave having a phase of $+\theta_s$ is generated with respect to the selected phase difference of $-\theta_s$ and supplied to the input terminal of the sensor amplifier circuit 200 to compensate for the phase difference created in the sensor amplifier circuit part 200 in the overall closed loop of the second circuit loop 124. Therefore, the second circuit loop 124 can sustain the self oscillation (S126).

Figure 17:
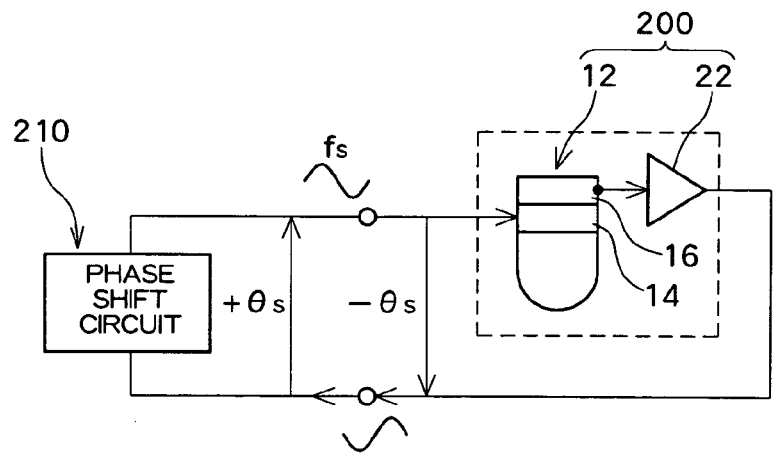
FIG. 17 illustrates a phase difference compensation for the second circuit loop in the hardness measurement system in the embodiment of the present invention.

This aspect is shown in FIG. 17. Here, the circuitry from the PLL circuit 190 to the sine wave generator 164 having the function to compensate for the selected phase difference $\theta_s$ is shown collectively as a phase shift circuit 210. As described hereinabove, the phase shift circuit 210 has a function to generate a sine wave having a phase of $+\theta_s$ with respect to the selected phase difference of $-\theta_s$ and supply it to the vibrator 14. Thus, if the phase shift circuit 210 is connected to the sensor amplifier circuit 200 to close the loop, the overall phase difference is compensated for and the self oscillation is sustained.

In this manner, when the self oscillation can be sustained within the closed loop under the vibration condition to be used for the hardness measurement, the object 8 is made to contact (S128) the hardness sensor 12 in this state. Then, as described with FIG. 11, the phase versus frequency characteristic of the hardness sensor 12 and the object 8 changes according to the hardness characteristic of the object 8 and the frequency is changed to compensate for the phase change Δθ according to the hardness. The frequency change is detected by a high-precision frequency counter 166 and output (S130) by a function of the frequency deviation output section 142. Then, from a function of the hardness converting section 144, the frequency deviation is converted to a hardness value (S132) in accordance with a predetermined conversion method.

Figure 18:
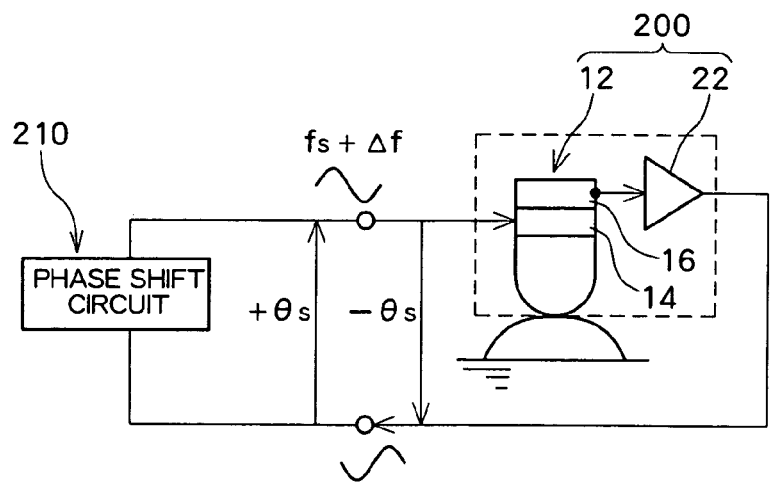
FIG. 18 illustrates a frequency deviation when the hardness sensor contacts the object in the hardness measurement system in the embodiment of the present invention.

This aspect is shown in FIG. 18. Here, the hardness sensor 12 contacts the object 8 in the state of FIG. 17. Then, from a function of the phase shift circuit 210, the hardness based phase difference Δθ is compensated for by changing the frequency by Δf so that the self oscillation frequency of the closed loop changes by Δf. The Δf corresponds to the frequency deviation, which is proportional to the hardness of the object 8.

In this manner, by using a phase shift circuit that maintains the phase difference between both ends of the hardness sensor by changing the frequency, a frequency and a phase difference are selected for use in the hardness measurement in the open loop. Then, the loop including the phase shift circuit can be closed from the vibration state in a short time and the self oscillation can be sustained in the vibration state. Therefore, the hardness of an object can be measured under vibration conditions suitable for use in hardness measurements.

What is claimed is:

1. A method for selecting an operating frequency for a hardness measurement system for measuring a hardness of an object from a change in frequency that occurs according to the hardness of the object and comprising a hardness sensor having a vibrator for applying vibrations to the object and a vibration detection sensor for detecting signals reflected from the object, and a phase shift circuit, which is connected in series with an amplifier to the hardness sensor, for changing a frequency and shifting a phase difference thereof to zero when a phase difference occurs between an input waveform to the vibrator and an output waveform from the vibration detection sensor, the method comprising:
   a peak detection step for detecting a plurality of peaks and distinguishing each peak in amplitude characteristic with respect to frequency or phase characteristic with respect to frequency, under a condition that the hardness sensor is in a free end state and not in contact with a test piece;
   a free end characteristic acquisition step for measuring and storing in a memory at least one of frequency, phase, or amplitude that changes at each peak position for the distinguished peaks;
   a contact characteristic acquisition step for measuring and storing in a memory at least one of frequency, phase, or amplitude that changes for each peak of the distinguished peaks when the hardness sensor is placed into contact with the test piece;
   a peak selection step for selecting a peak for use in hardness measurement on the basis of at least one of frequency change, phase change, or amplitude change between the free end characteristic acquisition step and the contact characteristic acquisition step for each peak of the distinguished peaks; and
   an operating frequency setting step for setting the frequency of the free end state of the selected peak as the operating frequency of the hardness sensor and setting a frequency separated by an arbitrary frequency width from the operating frequency of the hardness sensor as the operating frequency of the phase shift circuit.

2. A method for selecting an operating frequency for a hardness measurement system for measuring a hardness of an object from a change in frequency that occurs according to the hardness of the object and comprising a hardness sensor having a vibrator for applying vibrations to the object and a vibration detection sensor for detecting signals reflected from the object, and a phase shift circuit, which is connected in series with an amplifier to the hardness sensor, for changing a frequency and shifting a phase difference thereof to zero when a phase difference occurs between an input waveform to the vibrator and an output waveform from the vibration detection sensor, the method comprising:
   a peak detection step for detecting a plurality of peaks and distinguishing each peak in amplitude characteristic with respect to frequency or phase characteristic with respect to frequency under a condition that the hardness sensor is in a free end state and not in contact with a test piece;
   a free end characteristic acquisition step for measuring and storing in a memory at least one of frequency, phase, or amplitude that changes at each peak position for the distinguished peaks;
   a first characteristic acquisition step for measuring and storing in a memory at least one of frequency, phase, or amplitude that changes for each peak of the distinguished peaks when the hardness sensor is placed into contact with a soft first test piece;
   a second characteristic acquisition step for measuring and storing in a memory at least one of frequency, phase, or amplitude that changes for each peak of the distinguished peaks when the hardness sensor is placed into contact with a second test piece, which is harder than the first test piece;
   a peak selection step for selecting a peak for use in hardness measurement on the basis of at least one of frequency change, phase change, or amplitude change between the free end characteristic acquisition step and the first characteristic acquisition step for each peak of the distinguished peaks and at least one of frequency change, phase change, or amplitude change between the free end characteristic acquisition step and the second characteristic acquisition step for each peak of the distinguished peaks; and
   an operating frequency setting step for setting the frequency of the free end state of the selected peak as the operating frequency of the hardness sensor and setting a frequency separated by an arbitrary frequency width from the operating frequency of the hardness sensor as the operating frequency of the phase shift circuit.

3. An operating frequency selection method for a hardness measurement system according to claim 2, wherein:
   the peak selection step compares a direction of the frequency change and a direction of the phase change between the free end characteristic acquisition step and the first characteristic acquisition step and a direction of the frequency change and a direction of the phase change between the free end characteristic acquisition step and the second characteristic acquisition step and selects a peak from among candidate peaks changing in mutually opposite directions.

4. An operating frequency selection method for a hardness measurement system according to claim 3, wherein:
   the peak selection step selects from among candidate peaks for which a change in the first characteristic acquisition step compared to a change in the free end characteristic acquisition step in a decreasing direction for both frequency and phase and change in the second characteristic acquisition step compared to a change in the free end characteristic acquisition step in an increasing direction for both frequency and phase.

5. An operating frequency selection method for a hardness measurement system according to claim 3, wherein:
the peak selection step selects a peak having a large change amount from among candidate peaks.

6. An operating frequency selection method for a hardness measurement system according to claim 2, wherein:
the peak detection step further comprises a frequency limiting step for narrowing down a peak in an arbitrary frequency range from among the plurality of peaks.

7. An operating frequency selection method for a hardness measurement system according to claim 2, wherein:
the peak detection step further comprises a Q value limiting step for narrowing down a peak having a Q value that is less than or equal to an arbitrary Q value from among the plurality of peaks.

8. An operating frequency selection method for a hardness measurement system according to claim 2, wherein:
the peak detection step further comprises a phase change rate limiting step for narrowing down a peak that has a phase change rate less than or equal to an arbitrary value at a peak position from among the plurality of peaks.

9. An operating frequency selection method for a hardness measurement system according to claim 2, wherein:
the operating frequency setting step sets an arbitrary frequency width according to a Q value of the phase shift circuit.

10. An apparatus for selecting an operating frequency for a hardness measurement system for measuring a hardness of an object from a change in frequency that occurs according to the hardness of the object and comprising a hardness sensor having a vibrator for applying vibrations to the object and a vibration detection sensor for detecting signals reflected from the object, and a phase shift circuit, which is connected in series with an amplifier to the hardness sensor, for changing a frequency and shifting a phase difference thereof to zero when a phase difference occurs between an input waveform to the vibrator and an output waveform from the vibration detection sensor, the apparatus comprising:
peak detection section for detecting a plurality of peaks and distinguishing each peak in amplitude characteristic with respect to frequency or phase characteristic with respect to frequency under a condition that the hardness sensor is in a free end state and not in contact with a test piece;
free end characteristic acquisition section for measuring and storing in a memory at least one of frequency, phase, or amplitude that changes at each peak position for the distinguished peaks;
contact characteristic acquisition section for measuring and storing in a memory at least one of frequency, phase, or amplitude that changes for each peak of the distinguished peaks when the hardness sensor is placed into contact with the test piece;
peak selection section for selecting a peak for use in hardness measurement on the basis of at least one of frequency change, phase change, or amplitude change between the free end characteristic acquisition section and the contact characteristic acquisition section for each peak of the distinguished peaks; and
operating frequency setting section for setting the frequency of the free end state of the selected peak as the operating frequency of a hardness sensor and setting a frequency separated by an arbitrary frequency width from the operating frequency of the hardness sensor as the operating frequency of the phase shift circuit.

11. An apparatus for selecting an operating frequency for a hardness measurement system for measuring a hardness of an object from a change in frequency that occurs according to the hardness of the object and comprising a hardness sensor having a vibrator for applying vibrations to the object and a vibration detection sensor for detecting signals reflected from the object, and a phase shift circuit, which is connected in series with an amplifier to the hardness sensor, for changing a frequency and shifting a phase difference thereof to zero when a phase difference occurs between an input waveform to the vibrator and an output waveform from the vibration detection sensor, the apparatus comprising:
peak detection section for detecting a plurality of peaks and distinguishing each peak in amplitude characteristic with respect to frequency or phase characteristic with respect to frequency under a condition that the hardness sensor is in a free end state and not in contact with a test piece;
free end characteristic acquisition section for measuring and storing in a memory at least one of frequency, phase, or amplitude that changes at each peak position for the distinguished peaks;
first characteristic acquisition section for measuring and storing in a memory at least one of frequency, phase, or amplitude that changes for each peak of the distinguished peaks when the hardness sensor is placed into contact with a soft first test piece;
second characteristic acquisition section for measuring and storing in a memory at least one of frequency, phase, or amplitude that changes for each peak of the distinguished peaks when the hardness sensor is placed into contact with a second test piece, which is harder than the first test piece;
peak selection section for selecting a peak for use in hardness measurement on the basis of at least one of frequency change, phase change, or amplitude change between the free end characteristic acquisition section and the first characteristic acquisition section and at least one of frequency change, phase change, or amplitude change between the free end characteristic acquisition section and the second characteristic acquisition section for each peak of the distinguished peaks; and
operating frequency setting section for setting the frequency of the free end state of the selected peak as the operating frequency of the hardness sensor and setting the frequency separated by an arbitrary frequency width from the operating frequency of the hardness sensor as the operating frequency of the phase shift circuit.

12. An operating frequency selection apparatus for a hardness measurement system according to claim 11, wherein:
the peak selection section compare a direction of the frequency change and a direction of the phase change between the free end characteristic acquisition section and the first characteristic acquisition section and a direction of the frequency change and a direction of the phase change between the free end characteristic acquisition section and the second characteristic acquisition section and select a peak from among candidate peaks changing in mutually opposite directions.

13. An operating frequency selection apparatus for a hardness measurement system according to claim 12, wherein:
the peak selection section select from among candidate peaks for which a change in the first acquisition section compared to a change in the free end characteristic acquisition section in a decreasing direction for both frequency and phase and a change in the second characteristic acquisition section compared to a change in the free end characteristic acquisition section in an increasing direction for both frequency and phase.

14. An operating frequency selection apparatus for a hardness measurement system according to claim 12, wherein:
the peak selection section select a peak having a large change amount from among candidate peaks.

15. An operating frequency selection apparatus for a hardness measurement system according to claim 11, wherein:
the peak detection section further comprise frequency limiting section for narrowing down a peak in an arbitrary frequency range from among the plurality of peaks.

16. An operating frequency selection apparatus for a hardness measurement system according to claim 11, wherein:
the peak detection section further comprise Q value limiting section for narrowing down a peak having a Q value that is less than or equal to an arbitrary Q value from among the plurality of peaks.

17. An operating frequency selection apparatus for a hardness measurement system according to claim 11, wherein:
the peak detection section further comprise phase change rate limiting section for narrowing down a peak that has a phase change rate less than or equal to an arbitrary value at a peak position from among the plurality of peaks.

18. A hardness measurement system for measuring a hardness of an object using a hardness sensor comprising a vibrator for applying vibrations to the object and a vibration detection sensor for detecting signals reflected from the object, the system comprising:
a first circuit loop, which is an open loop with a sensor amplifier circuit part that the hardness sensor connecting an amplifier in series, that operates in a state where a sweeping signal with changing frequency is input from an external source, a plurality of peaks appearing in amplitude characteristic with respect to frequency or phase characteristic with respect to frequency are compared to a predetermined criterion and a peak for use in hardness measurement is selected, a selected frequency corresponding to the selected peak is input by the sensor amplifier circuit part, and a selected phase difference corresponding to the selected frequency is output;
a second circuit loop, which is a closed loop and in which a phase shift circuit is connected between an input terminal and an output terminal of the sensor amplifier circuit part to close the second circuit loop to form a self oscillating loop, for sustaining self oscillation by changing the frequency and shifting the phase difference thereof to zero by the phase shift circuit when the phase difference occurs between an input waveform to and an output waveform from the sensor amplifier circuit part;
switching section for switching a circuit loop, which includes the sensor amplifier circuit part, from an operating state under the selected frequency and the selected phase difference in the first circuit loop to an operating state where the selected phase difference across both terminals of the sensor amplifier circuit part in the second circuit loop is compensated for by the phase shift circuit and the self oscillation is sustained under the selected frequency; and
a frequency deviation output section for outputting a frequency deviation that changed from the selected frequency and compensated a phase difference component based on hardness by the phase shift circuit so that the selected phase difference maintained across both terminals of the sensor amplifier circuit part, where the phase difference component is the phase difference across both terminals of the sensor amplifier circuit part that changes further from the selected phase difference according to the hardness of the object when the hardness sensor is placed in contact with the object after the switching a circuit loop.

19. A hardness measurement system according to claim 18, wherein the phase shift circuit comprises:
a phase locked circuit, in which a phase detector, a voltage controlled oscillator, and a divider are connected in a loop configuration, for locking an oscillation state so that the phase difference between two input of the phase detector is zero where the output of the sensor amplifier circuit part having the selected phase difference and the output of the divider are input to the phase detector; and
a compensation signal output section for performing compensation computations on data corresponding to the selected phase difference for a real time detailed data from the divider and accordingly outputting a phase difference compensation signal that compensates an amount of the selected phase difference for one period of an output signal from the sensor amplifier circuit part, and the phase difference compensation signal provides to the sensor amplifier circuit part as an input signal of the sensor amplifier circuit part.

20. A hardness measurement system according to claim 19 wherein: including
a converter for converting the output of the sensor amplifier circuit part into a digital signal and supplying to the phase shift circuit; and
the compensation signal output section of the phase shift circuit operating from digital signals to further include:
a divider counter for counting data signals of the voltage controlled oscillator;
a full adder circuit for adding data that compensates for the selected phase difference and has the same number of bits as the number of bits of divider counter, to the divider counter data; and
a waveform generator for generating a sine wave signal from data from the full adder circuit, and the generated sine wave signal provide to the sensor amplifier circuit part as the phase difference compensation signal.

* * * * *

UNITED STATES PATENT AND TRADEMARK OFFICE
CERTIFICATE OF CORRECTION

PATENT NO. : 7,565,841 B2  
APPLICATION NO. : 11/547446  
DATED : July 28, 2009  
INVENTOR(S) : Sadao Omata et al.

Page 1 of 1

It is certified that error appears in the above-identified patent and that said Letters Patent is hereby corrected as shown below:

On the Title Page

Please delete the following:

Item  
"(86) PCT No.: PCT/JP2004/018577

§ 371 (c)(1),  
(2), (4) Date: April 30, 2007"

and Replace with:

-- (86) PCT No.: PCT/JP2004/018577

§ 371 (c)(1),  
(2), (4) Date: November 1, 2006 --

Signed and Sealed this

Fifteenth Day of September, 2009

David J. Kappos  
*Director of the United States Patent and Trademark Office*